(12) United States Patent
Kannan et al.

(10) Patent No.: US 8,592,562 B2
(45) Date of Patent: Nov. 26, 2013

(54) METHOD FOR MAKING ANTIBODY FC-HETERODIMERIC MOLECULES USING ELECTROSTATIC STEERING EFFECTS

(75) Inventors: Gunasekaran Kannan, Issaquah, WA (US); Michael Wittekind, Bainbridge Island, WA (US); Wei Yan, Sammamish, WA (US); Martin Pentony, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 332 days.

(21) Appl. No.: 12/811,207

(22) PCT Filed: Jan. 6, 2009

(86) PCT No.: PCT/US2009/000071
§ 371 (c)(1),
(2), (4) Date: Jun. 29, 2010

(87) PCT Pub. No.: WO2009/089004
PCT Pub. Date: Jul. 16, 2009

(65) Prior Publication Data
US 2010/0286374 A1 Nov. 11, 2010

Related U.S. Application Data

(60) Provisional application No. 61/019,569, filed on Jan. 7, 2008, provisional application No. 61/120,305, filed on Dec. 5, 2008.

(51) Int. Cl.
*C07K 16/00* (2006.01)
*C07H 21/04* (2006.01)
*C12N 15/63* (2006.01)
*C12N 5/10* (2006.01)

(52) U.S. Cl.
USPC ............................................ 530/387.3

(58) Field of Classification Search
USPC ............................................ 530/387.3
See application file for complete search history.

(56) References Cited

U.S. PATENT DOCUMENTS

| | | | |
|---|---|---|---|
| 2004/0253238 A1* | 12/2004 | Bogen et al. | 424/144.1 |
| 2006/0074225 A1 | 4/2006 | Chamberlain et al. | |
| 2010/0015133 A1 | 1/2010 | Igawa et al. | |
| 2012/0149876 A1 | 6/2012 | Von Kreudenstein et al. | |
| 2013/0039913 A1 | 2/2013 | Labrijn et al. | |

FOREIGN PATENT DOCUMENTS

| | | |
|---|---|---|
| EP | 1870459 | 12/2007 |
| EP | 1 999 154 B1 | 10/2012 |
| WO | 2006/106905 | 10/2006 |
| WO | 2007/110205 | 10/2007 |
| WO | 2010/063785 | 6/2010 |
| WO | WO 2010/063785 A2 | 6/2010 |

OTHER PUBLICATIONS

Gunasekaran et al. (JBC 285(25):19637-19646 (2010)).*
Ibragimova and Eade (Biophysical Journal, Oct. 1999, vol. 77, pp. 2191-2198).*
Burgess et al, ( Journal of Cell Biology vol. 111 Nov. 1990 2129-2138).*
Lazar et al (Molecular and Cellular Biology Mar. 1988 vol. 8 No. 3 1247-1252).*
Schwartz et al, Proc Natl Acad Sci USA vol. 84:6408-6411 (1987)).*
Lin et al Biochemistry USA vol. 14:1559-1563 (1975)).*
Salfeld (Nature Biotech. 25(12): 1369-1372 (2007)).*
Dall'Acqua (J. Immunol. 177:1129-1138 (2006)).*
Bogan and Thorn, "Anatomy of hot spots in protein interfaces," J Mol Biol 280:1-9, 1998.
Gabdoulline and Wade, "Biomolecular diffusional association," Curr Opin Struct Biol 12:204-213, 2002.
Halperin et al., "Protein-protein interactions: coupling of structurally conserved residues and of hot spots across interfaces. Implications for docking," Structure 12:1027-1038, 2004.
Joachimiak et al., "Computational design of a new hydrogen bond network and at least a 300-fold specificity switch at a protein-protein interface," J Mol Biol 361:195-208, 2006.
Kortemme and Baker, "Computational design of protein-protein interactions," Curr Opin Chem Biol 8:91-97, 2004.
Kortemme et al., "Computational redesign of protein-protein interaction specificity," Nat Struct Biol 11:371-379, 2004.
Marvin and Lowman, "Redesigning an antibody fragment for faster association with its antigen," Biochemistry 42:7077-7083, 2003.
Nohaile et al., "Altering dimerization specificity by changes in surface electrostatics," Proc Natl Acad Sci USA 98 (6):3109-3114, 2001.
Ridgway et al., "'Knobs-into-holes' engineering of antibody CH3 domains for heavy chain heterodimerization," Protein Eng Des Sel 9(7):617-621, 1996.
Schreiber, "Electrostatic design of protein-protein association rates," Methods Mol Biol 340:235-249, 2006.
Selzer et al., "Rational design of faster associating and tighter binding protein complexes," Nat Struct Biol 7:537-541, 2000.
Sheinerman et al., "Electrostatic aspects of protein-protein interactions," Curr Opin Struct Biol 10:153-159, 2000.
Sinha and Smith-Gill, "Electrostatics in protein binding and function," Curr Protein Pept Sci 3: 601-614, 2002.
Szczepek et al., Structure-based redesign of the dimerization interface reduces the toxicity of zinc-finger nucleases, Nat Biotechnol 25:786-793, 2007.
Zhu et al., "Remodeling domain interfaces to enhance heterodimer formation," Protein Sci 6:781-788, 1997.

* cited by examiner

*Primary Examiner* — Lynn Bristol
(74) *Attorney, Agent, or Firm* — Thomas J. Wrona

(57) ABSTRACT

The invention relates to methods of making Fc-heterodimeric proteins or polypeptides. The invention also relates to the Fc-heterodimeric proteins or polypeptides themselves, including the individual polypeptide components that comprise the heterodimer. Nucleic acids encoding such polypeptides, expression vectors, and host cells. Moreover, the invention relates to pharmaceutical compositions comprising one of more Fc-heterodimeric proteins or polypeptides.

18 Claims, 12 Drawing Sheets

(a)

```
                340        350        360        370        380        390
IGG1_HUMAN  AKGQPREPQVYTLPPSR DELTK NQVSLTCLVKGFYPSDIAVEWESNGQPENNY KTT PPVL
IGG2_HUMAN  TKGQPREPQVYTLPPSR EEMTK NQVSLTCLVKGFYPSDIAVEWESNGQPENNY KTT PPML
IGG3_HUMAN  TKGQPREPQVYTLPPSR EEMTK NQVSLTCLVKGFYPSDIAVEWESSGQPENNY NTT PPML
IGG4_HUMAN  AKGQPREPQVYTLPPSQ EEMTK NQVSLTCLVKGFYPSDIAVEWESNGQPENNY KTT PPVL
             *********** **** *  * ************** ************* **  ***** **

400        410        420        430        440
IGG1_HUMAN  DSDGSFFLYSK LTVDK SRWQQGNVFSCSVMHEALHNHYTQ KSLSLSPGK
IGG2_HUMAN  DSDGSFFLYSK LTVDK SRWQQGNVFSCSVMHEALHNHYTQ KSLSLSPGK
IGG3_HUMAN  DSDGSFFLYSK LTVDK SRWQQGNIFSCSVMHEALHNRFTQ KSLSLSPGK
IGG4_HUMAN  DSDGSFFLYSR LTVDK SRWQEGNVFSCSVMHEALHNHYTQ KSLSLSLGK
             *********** ***** **** ** *************** ** ****** **
```

(b)

```
IGG1_MOUSE   TKGRPKAPQVYTIPPPK EQMAK DKVSLTCMITDFFPEDITVEWQWNGQPAENY KNTQPIM
IGG2A_MOUSE  PKGSVRAPQVYVLPPPE EEMTK KQVTLTCMVTDFMPEDIYVEWTNNGKTELNY KNTEPVL
IGG2B_MOUSE  IKGLVRAPQVYTLPPPA EQLSR KDVSLTCLVVGENPGDISVEWTSNGHTEENY KDTAPVL
IGG3_MOUSE   PKGRAQTPQVYTIPPPR EQMSK KKVSLTCLVTNFFSEAISVEWERNGELEQDY KNTPPIL
              *  ***** ****** **   * ***** ********* ****** **  **** *

IGG1_MOUSE   NTNGSYFVYSK LNVQK SNWEAGNTFTCSVLHEGLHNHHTEKS LSHS
IGG2A_MOUSE  DSDGSYFMYSK LRVEK KNWVERNSYSCSVVHEGLHNHHTTKS FSRT
IGG2B_MOUSE  DSDGSYFIYSK LNMKT SKWEKTDSFSCNVRHEGLKNYYLKKT ISRS
IGG3_MOUSE   DSDGTYFLYSK LTVDT DSWLQGEIFTCSVHEALHNHHTQ KNLSRS
              ** **   **  *  *          * *  *  *
```

FIGURE 4A (c)

```
IGA_HUMAN    -SGNT-FRPEVHLLPPPSEELALNELVTLTCLARGFSPKDVLVRWLQGSQELPREKYLTW
IGE_HUMAN    TSGPR-AAPEVYAFATPEWPGSRDK-RTLACLIQNFMPEDISVQWLHNEVQLPDARHSTT
IGD_HUMAN    REPAA-QAPVKLSLNLLASSDPPEAASWLLCEVSGFSPPNILMWLEDQREVNTSGFAPA
IGM_HUMAN    PKGVALHRPDVYLLPPAREQLNLRESATITCLVTGFSPADVFVQWMQRGQPLSPEKYVTS
                *           *        ****      *    *     *   *   *

IGA_HUMAN    ASRQEPSQGTTTFAVTSILRVAAEDWKKGDTFSCMVGHEAL-PLAFTQKTIDRLAGK
IGE_HUMAN    QPRKT---KGSGFFVFSRLEVTRAEWEQKDEFICRAVHEAASPSQTVQRAVSVNPGK
IGD_HUMAN    RPPPQP---GSTTFWAWSVLRVPAPPSPQPATYTCVVSHEDSRTLLNASRSLEVSYVT
IGM_HUMAN    APMPEP-QAPGRYFAHSILTVSEEEWNTGETYTCVVAHEAL-PNRVTERTVDKSTGK
                 *    *        *                    *
```

FIGURE 4B

K409E & D399K Mutations as An Example for Promoting Homodimers

METHOD FOR MAKING ANTIBODY FC-HETERODIMERIC MOLECULES USING ELECTROSTATIC STEERING EFFECTS

CROSS-REFERENCE TO RELATED APPLICATIONS

This application is a National Stage application under 35 U.S.C. §371 of International Application No. PCT/US2009/000071 (which designated the United States), having an international filing date of Jan. 6, 2009, which claims the benefit of U.S. provisional patent application No. 61/019,569 filed Jan. 7, 2008 and U.S. provisional patent application No. 61/120,305 filed Dec. 5, 2008, each of which is explicitly incorporated herein by reference in its entirety for all purposes.

REFERENCE TO THE SEQUENCE LISTING

The present application is being filed along with a Sequence Listing in electronic format. The Sequence Listing is provided as a file entitled A-1392-US-PCT_ST25.txt, created Jun. 28, 2010, which is 49 KB in size. The information in the electronic format of the Sequence Listing is incorporated herein by reference in its entirety.

BACKGROUND

Antibodies have become the modality of choice within the biopharma industry because they possess several characteristics that are attractive to those developing therapeutic molecules. Along with the ability to target specific structures or cells, antibodies make its target susceptible to Fc-receptor cell-mediated phagocytosis and killing (Raghavan and Bjorkman 1996). Further, the antibody's ability to interact with neonatal Fc-receptor (FcRn) in a pH dependent manner confers it with extended serum half-life (Ghetie and Ward 2000). This unique feature of antibodies allows extending the half-life of therapeutic protein or peptide in the serum by engineering Fc-fusion molecules.

Antibodies belong to the immunoglobulin class of proteins which includes IgG, IgA, IgE, IgM, and IgD. The most abundant immunoglobulin class in human serum is IgG whose schematic structure is shown in the FIG. 1 (Deisenhofer 1981; Huber 1984; Roux 1999). The IgG structure has four chains, two light and two heavy chains; each light chain has two domains and each heavy chain has four domains. The antigen binding site is located in the Fab region (Fragment antigen binding) which contains a variable light (VL) and a variable heavy (VH) chain domain as well as constant light (LC) and constant heavy (CH1) chain domains. The CH2 and CH3 domain region of the heavy chain is called Fc (Fragment crystallizable). The IgG molecule can be considered as a heterotetramer having two heavy chains that are held together by disulfide bonds (—S—S—) at the hinge region and two light chains. The number of hinge disulfide bonds varies among the immunoglobulin subclasses (Papadea and Check 1989). The FcRn binding site is located in the Fc region of the antibody (Martin, West et al. 2001), and thus the extended serum half-life property of the antibody is retained in the Fc fragment. The Fc region alone can be thought of as a homodimer of heavy chains comprising CH2 and CH3 domains.

In certain instances, it is desirable to create a molecule that contains the Fc portion of an antibody but comprises a heterodimer. An important application of Fc heterodimeric molecules is the generation of bispecific antibodies (BsAbs). Bispecific antibodies refer to antibodies having specificities for at least two different antigens (Nolan and O'Kennedy 1990; de Leij, Molema et al. 1998; Carter 2001). Instead of having identical sequence in both the Fabs, bispecific antibodies bear different sequences in the two Fabs so that each arm of the Y-shaped molecule can bind to different antigens.

The use of bispecific antibodies for immunotherapy of cancer has been extensively reviewed in the literature (for example, see (Nolan and O'Kennedy 1990; de Leij, Molema et al. 1998; Carter 2001)). By having the ability to bind to two different epitopes or molecules, BsAbs provide means to both trigger an immune effector cell and bind a surface antigen on a tumor target cell. This helps to make use of the immune system to destroy cancer cells. Other applications of bispecific antibodies are extensively covered in U.S. Pat. Nos. 5,731,168 and 7,183,076.

The classical method of producing BsAbs by co-expressing two different IgGs in hybrid hybridomas leads to up to 10 possible combinations of heavy and light chains. This compromises the yield and imposes a purification challenge. Carter and co-workers engineered heavy chains for heterodimerization using a "knobs-into-holes" strategy (Ridgway, Presta et al. 1996; Atwell, Ridgway et al. 1997; Merchant, Zhu et al. 1998; Carter 2001). The knobs-into-holes concept was originally proposed by Crick as a model for packing of amino acid side chains between adjacent α-helices (Crick 1952). Carter and co-workers created a knob at the CH3 domain interface of the first chain by replacing a smaller amino acid side chain with a larger one (for example, T366Y); and a hole in the juxtaposed position at the CH3 interface of the second chain was created by replacing a larger amino acid side chain with a smaller one (for example, Y407T). The basis for creating knob and hole in the juxtaposed positions is that the knob and hole interaction will favor heterodimer formation, whereas the knob-knob and the hole-hole interaction will hinder homodimers formation due to the steric clash and deletion of favorable interactions, respectively. The knobs-into-holes mutations were also combined with inter-CH3 domain disulfide bond engineering to enhance heterodimer formation (Sowdhamini, Srinivasan et al. 1989; Atwell, Ridgway et al. 1997). In addition to these mutations, the input DNA ratio was also varied to maximize the yield (Merchant, Zhu et al. 1998). The "knobs-into-holes" technique is disclosed in U.S. Pat. Nos. 5,731,168 and 7,183,076.

SUMMARY

This application describes a strategy for altering the interaction of antibody domains, e.g., altering a CH3 domain to reduce the ability of the domain to interact with itself, i.e., form homodimers. In particular, one or more residues that make up the CH3-CH3 interface is replaced with a charged amino acid such that the interaction becomes electrostatically unfavorable. In preferred embodiments, a positive-charged amino acid in the interface, such as a lysine, arginine, or histidine, is replaced with a negative charged amino acid, such as aspartic acid or glutamic acid. In other embodiments, a negative-charged amino acid in the interface is replaced with a positive-charged amino acid. In certain embodiments, the amino acid is replaced with an unnatural amino acid having the desired charge characteristic.

Further described herein is a strategy for altering a pair of CH3 domains to reduce the ability of each domain to interact with itself but to increase the ability of the domains to interact with each other, i.e., form heterodimers. This can be achieved by replacing one or more residues that make up the CH3-CH3 interface in both CH3 domains with a charged amino acid such that homodimer formation is electrostatically unfavorable but heterodimerization is electrostatically favorable. In certain embodiments, a charged amino acid in each CH3 domain is replaced with an amino acid with an opposite charge. For example, a positive-charged amino acid may be replaced with a negative charged amino acid in the first CH3 domain and a negative charged amino acid may be replaced with a positive-charged amino acid in the second CH3 domain. By reversing the charge of the amino acid, homodimer formation is reduced. When the replacements are coordinated properly, the reversed charges are electrostatically favorable, i.e., opposing charges in the interface, for heterodimerization formation.

In certain aspects, the invention provides a method of preparing a heterodimeric protein. The heterodimer may comprise a first CH3-containing polypeptide and a second CH3-containing polypeptide that meet together to form an interface engineered to promote heterodimer formation. The first CH3-containing polypeptide and second CH3-containing polypeptide are engineered to comprise one or more charged amino acids within the interface that are electrostatically unfavorable to homodimer formation but electrostatically favorable to heterodimer formation.

Such methods may include culturing a host cell comprising nucleic acids encoding the first and second CH3-containing polypeptides such that the polypeptides are co-expressed by the cell. In certain embodiments, the nucleic acids encoding the first and the second CH3-containing polypeptides are provided to the host cell at a ratio, for example 1:1, 1:2, 2:1, 1:3, 3:1, 1:4, 4:1, 1:5, 5:1, 1:6, 6:1, 1:7, 7:1, 1:8, 8:1, 1:9, 9:1, 1:10, 10:1. It is contemplated that altering the ratio of nucleic acids may increase the production of heterodimeric molecules versus homodimeric molecules.

The heterodimeric molecules may be purified from the host-cell culture using standard techniques. For example, when the heterodimeric protein comprises an Fc, the protein may be purified using a Protein A column. The purification techniques include but are not limited to chromatographic methods such as size exclusion, ion exchange and affinity-based chromatography and ultracentrifugation.

In certain embodiments, the CH3-containing polypeptide comprises an IgG Fc region, preferably derived from a wild-type human IgG Fc region. By "wild-type" human IgG Fc it is meant a sequence of amino acids that occurs naturally within the human population. Of course, just as the Fc sequence may vary slightly between individuals, one or more alterations may be made to a wild-type sequence and still remain within the scope of the invention. For example, the Fc region may contain additional alterations that are not related to the present invention, such as a mutation in a glycosylation site, inclusion of an unnatural amino acid, or a "knobs-into-holes" mutation.

In certain embodiments, the polypeptide containing the CH3 region is an IgG molecule and further contains a CH1 and CH2 domain. Exemplary human IgG sequences comprise the constant regions of IgG1 (e.g., SEQ ID NO:3; CH1=amino acids 1-98, CH2=amino acids 111-223, CH3=224-330), IgG2 (e.g., SEQ ID NO:4; CH1=amino acids 1-94, CH2=amino acids 111-219, CH3=220-326), IgG3 (e.g., SEQ ID NO:5; CH1=amino acids 1-98, CH2=amino acids 161-270, CH3=271-377), and IgG4 (e.g., SEQ ID NO:6; CH1=amino acids 1-98, CH2=amino acids 111-220, CH3=221-327). Those of skill in the art may differ in their understanding of the exact amino acids corresponding to the various domains of the IgG molecule. Thus, the N-terminus or C-terminus of the domains outlined above may extend or be shortened by 1, 2, 3, 4, 5, 6, 7, 8, 9, or even 10 amino acids. Also note that the numbering scheme used here to designate domains differ from the EU numbering scheme of Kabat that is used in the rest of this patent application. For example, IgG1 "CH3=224-330" corresponds to "CH3=341-447" in EU numbering scheme.

The Fc region also may be comprised within the constant region of an IgA (e.g., SEQ ID NO:7), IgD (e.g., SEQ ID NO:8), IgE (e.g., SEQ ID NO:9), and IgM (e.g., SEQ ID NO:10) heavy chain.

The polypeptide containing the CH3 region may be an antibody heavy chain and the host cell may further express one or more antibody light chains. In embodiments wherein more than one heavy chain and light chains are co-expressed (e.g., bivalent antibody), each heavy chain may comprise a mutation in the CH1 region and each light chain may comprise a mutation in the constant region to preferentially bind to each other but not bind to the other light or heavy chain, respectively. In preferred embodiments, such mutations involve altering the charge of one or more amino acids in the interface between the CH1 region and the constant region of a light chain.

Preferred embodiments of the invention include but are not limited to an antibody, a bispecific antibody, a monospecific monovalent antibody, a bispecific maxibody (maxibody refers to scFv-Fc), a monobody, a peptibody, a bispecific peptibody, a monovalent peptibody (a peptide fused to one arm of a heterodimeric Fc molecule), and a receptor-Fc fusion protein. See FIG. 2.

Examples of mammalian host cells that may be used include but are not limited to CHO, 293, and myeloma cell lines. The host cell may also be yeast or a prokaryote, such as *E. coli*.

The heterodimeric proteins may be particularly useful in therapeutic compositions. In certain embodiments, a heterodimeric protein may be formulated in a composition that includes one or more pharmaceutically acceptable buffer or excipient. Such therapeutic composition may be administered to a subject to treat a disease or may be given to prevent a disease or prevent the symptoms of a disease from progressing.

Solvent exposed or structurally not conserved residues are shown in the stick representation. The analysis is based on the IgG1 crystal structure (PDB code: 1L6X) which is determined at high-resolution (1.65 Å) (Idusogie, Presta et al. 2000).

FIG. 4A-4B. Comparison of IgG subclass sequences from (a) human and (b) mouse. Only the heavy chain sequence corresponding to the CH3 domain is shown. The star (*) indicates residue positions involved in the CH3-CH3 domain interaction identified based on the IgG1 human Fc crystal structure (1L6X). Positions marked with rectangles are preferred residues for mutation to enhance heterodimer formation. It may be noted here that charged residues are highly conserved among the IgGs. (c) CH3 domain sequence comparison of other class of antibodies (IgA, IgE, IgD, and IgM). The interface residue positions (indicated by "*") in (b) and (c) were identified based on sequence comparison with Hu IgG1 sequence that is also shown. In (a), the sequences derived from human IgG1, IgG2, IgG3, and IgG4 correspond to SEQ ID NO:11, SEQ ID NO:12, SEQ ID NO:13, and SEQ ID NO:14, respectively. In (b), the sequences derived from human IgG1, mouse IgG1, mouse IgG2a, mouse IgG2b, and mouse IgG3 correspond to SEQ ID NO:15, SEQ ID NO:16, SEQ ID NO:17, SEQ ID NO:18, and SEQ ID NO:19, respectively. In (c), the sequences derived from human IgG1, human IgA, human IgE, human IgD, and human IgM correspond to SEQ ID NO:20, SEQ ID NO:21, SEQ ID NO:22, SEQ ID NO:23, and SEQ ID NO:24, respectively.

Figure 5:
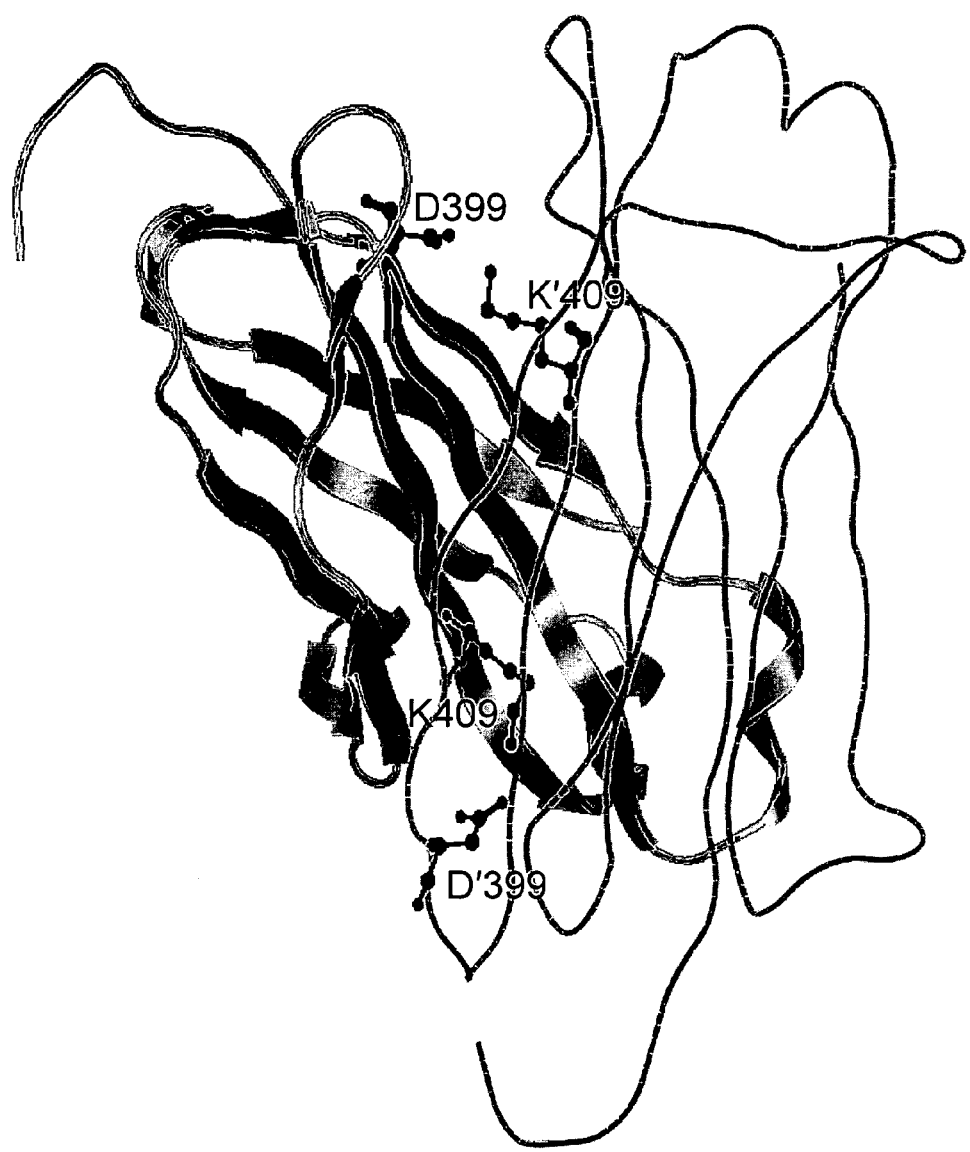

FIG. 5. Crystal structure of CH3 domain homodimer with one domain shown in ribbon representation and the other domain shown in wire model. The Lys409 (Lys409' in the second domain) and Asp399 (Asp399' in the second) residues are shown in ball-and-stick model in order to illustrate each pair-wise interaction is represented twice in the structure. This is due to the two-fold symmetry present in the CH3-CH3 domain interaction. The figure was created using the 1L6X co-ordinates deposited in the PDB.

Figure 6:
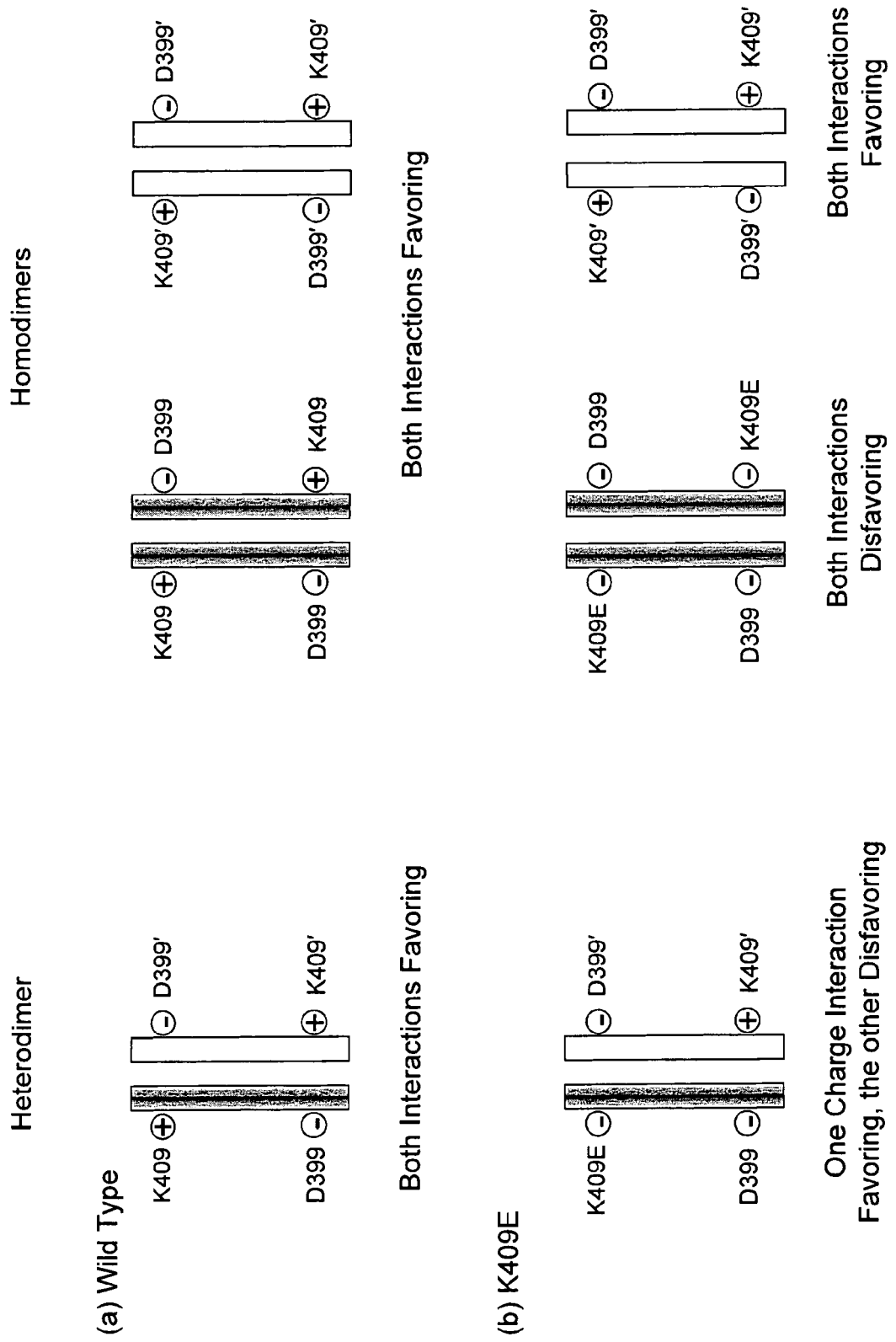

FIG. 6. Schematics showing electrostatic interactions in the wild type and in the mutants designed as an example to enhance heterodimer formation and hinder homodimer formation. (a) In the case of WT, electrostatic interactions favor both heterodimer and homodimer formation giving them equal probability. (b) In the single mutant (K409E) case, one of the homodimer is discouraged by both the interactions and at the same time heterodimer is also discouraged by one of the interactions. In the double mutant case, both the electrostatic interactions favor heterodimer and disfavor homodimer formation. Additional mutations involving charge change (for example, K360E) could also be used to enhance the electrostatic steering effects on the formation of heterodimer and homodimer.

Figure 7:
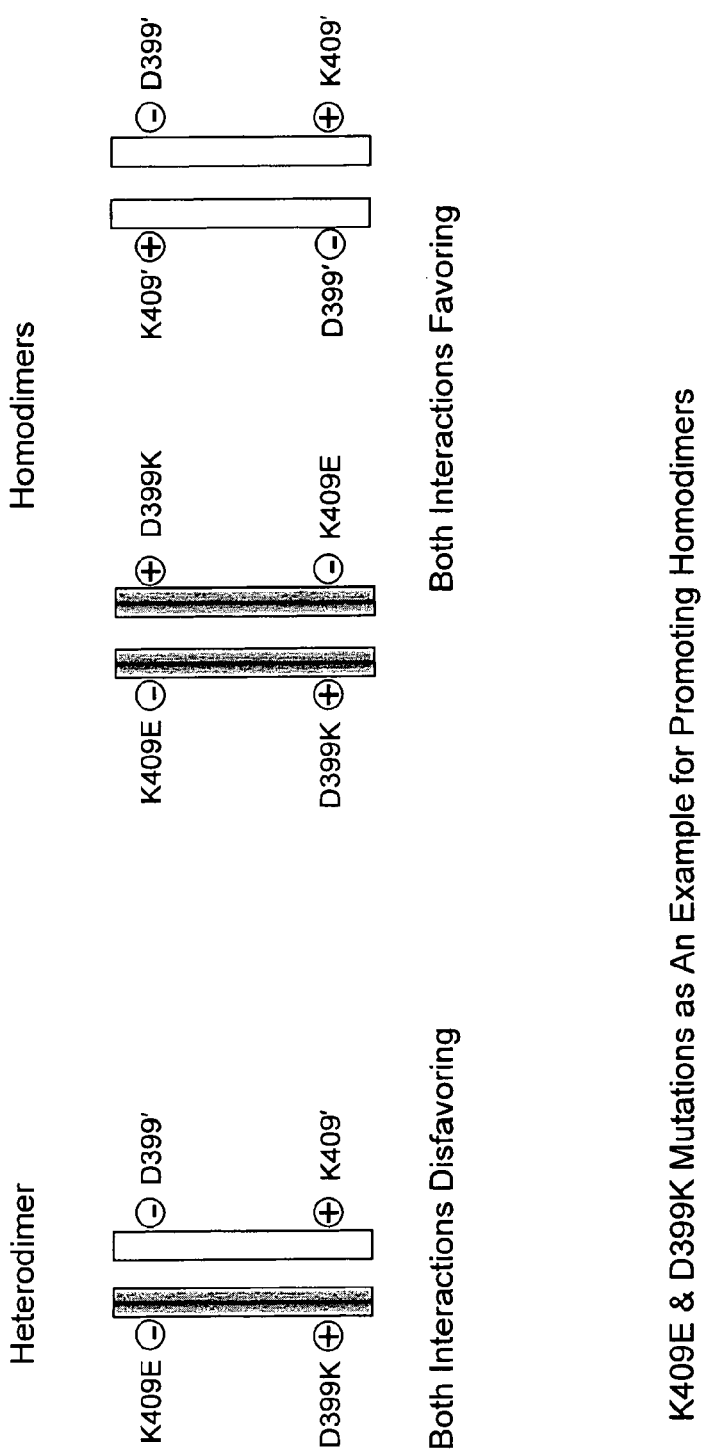

FIG. 7. This figure shows that electrostatic interactions could also be used to favor homodimers and disfavor heterodimer formation, when two different chains are co-expressed.

Figure 8:
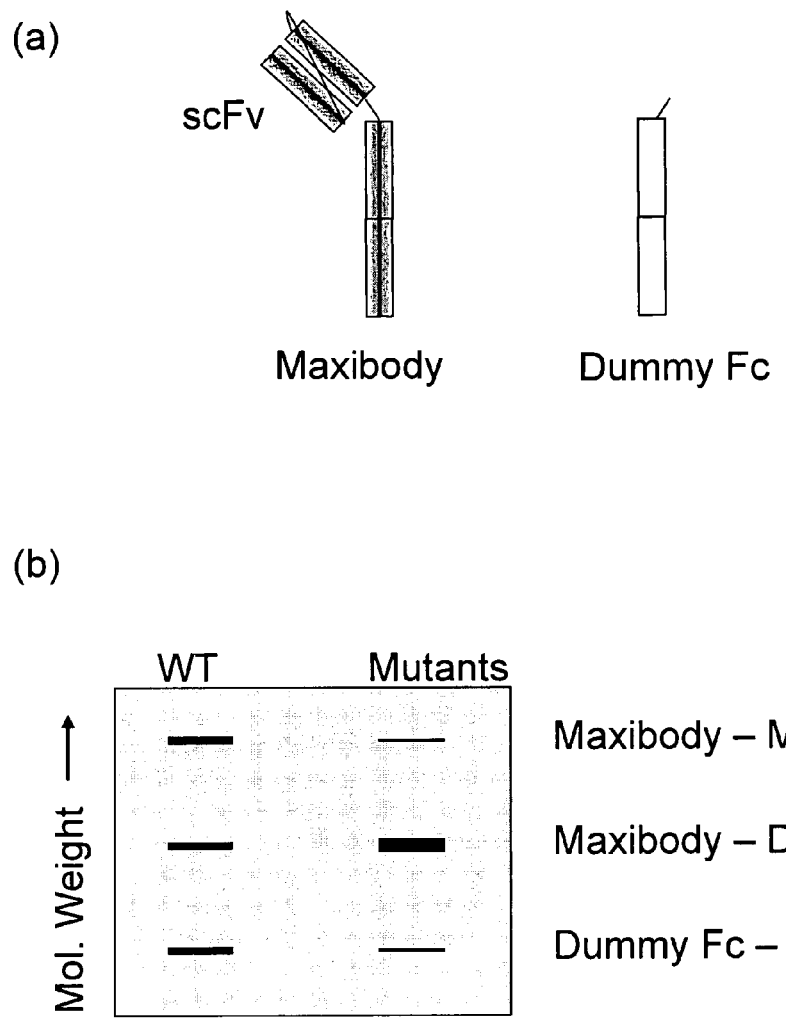

FIG. 8. Figure (a) shows the schematic drawing of the constructs used in the Example. The first chain of the Fc has a maxibody (single chain fragment variable, scFv) covalently linked, and the second chain called dummy Fc does not have any domain or functionality attached to it. (b) Illustration of expected relative mobility on the SDS-PAGE. Because the Fc chain attached to the maxibody has a higher molecular weight than the dummy Fc, homodimers and heterodimer have different mobility on the SDS-PAGE. The thickness of the band on the SDS-PAGE can be used as a measure of fraction of heterodimer and homodimer yield. The wild type is included as a control and to monitor relative improvement on the heterodimer yield due to various mutations.

Figure 9:
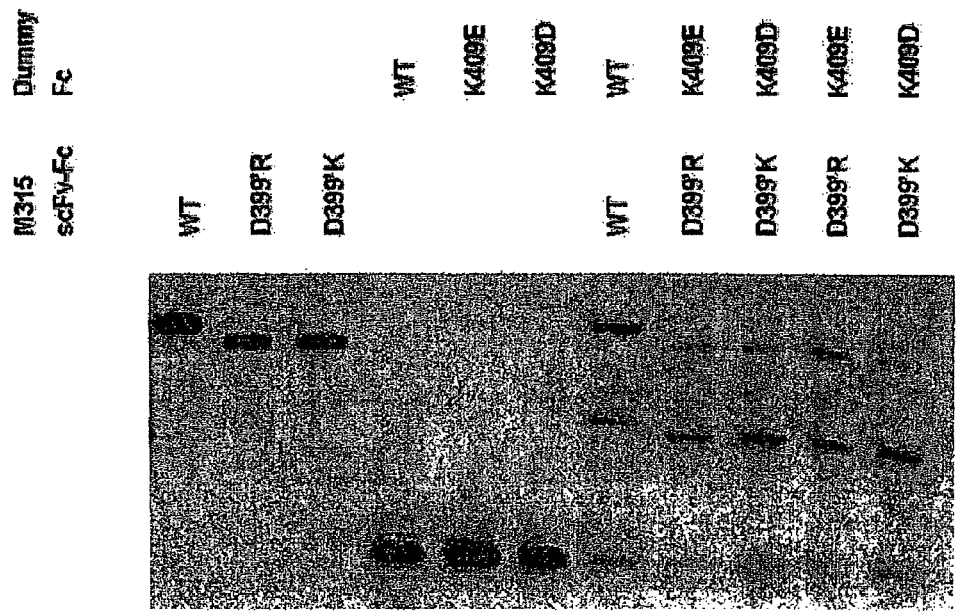

FIG. 9. SDS-PAGE analysis showing the effects of mutations on the D399' - - - K409 interaction pair.

Figure 10:
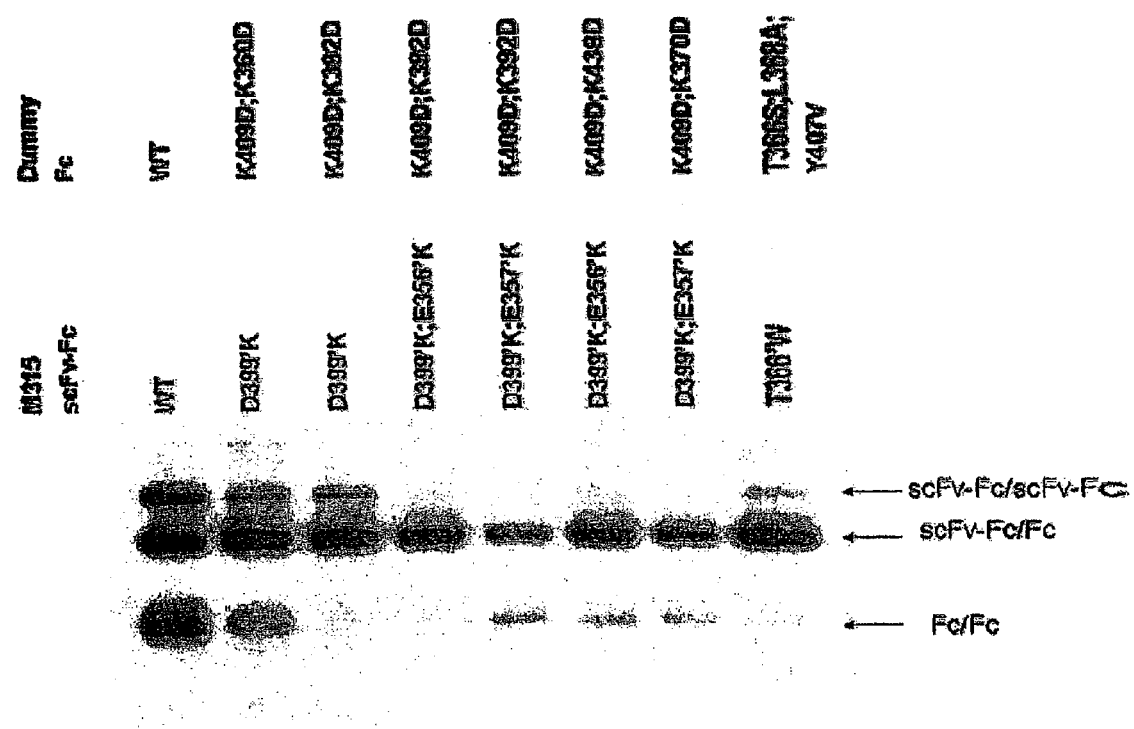

FIG. 10. SDS-PAGE analysis of charge residue mutations (listed in Table 6) in addition to D399'K - - - K409D pair mutations. Wild type (first lane) and knobs-into-holes mutations (last lane) are also shown for comparison. 1:2 input DNA ratio of dummy Fc and M315 maxibody was used here.

Figure 11:
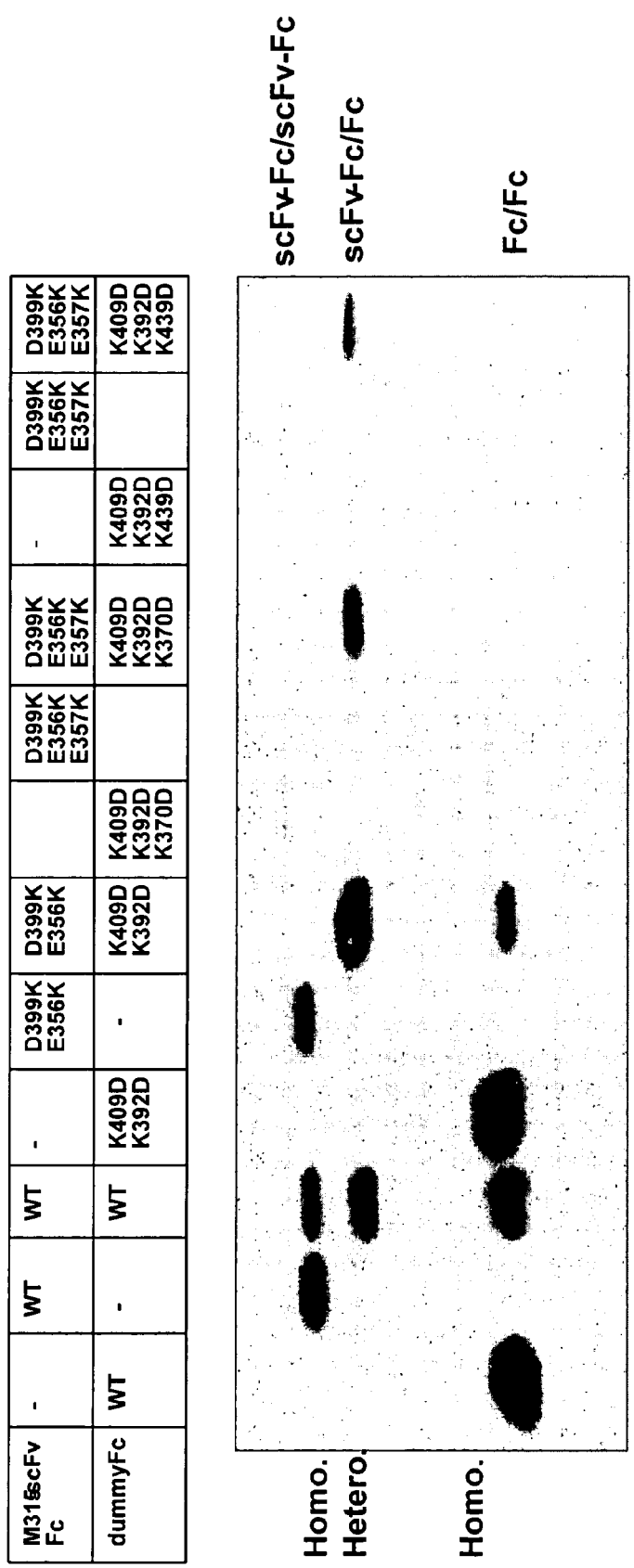

FIG. 11. Western blot demonstrating certain combinations of mutant achieve high selectivity for heterodimer formation. Fc molecules were detected using goat-anti-human Fc HRP conjugated at 1:10,000.

DETAILED DESCRIPTION OF PREFERRED EMBODIMENTS

A total of 48 antibody crystal structures which had co-ordinates corresponding to the Fc region were identified from the Protein Data Bank (PDB) (Bernstein, Koetzle et al. 1977) using a structure based search algorithm (Ye and Godzik 2004). Examination of the identified Fc crystal structures revealed that the structure determined at highest resolution corresponds to the Fc fragment of RITUXIMAB bound to a minimized version of the B-domain from protein A called Z34C(PDB code: 1L6X). The biological Fc homodimer structure for 1L6X was generated using the deposited Fc monomer co-ordinates and crystal symmetry. Two methods were used to identify the residues involved in the CH3-CH3 domain interaction: (i) contact as determined by distance limit criterion and (ii) solvent accessible surface area analysis.

According to the contact based method, interface residues are defined as residues whose side chain heavy atoms are positioned closer than a specified limit from the heavy atoms of any residues in the second chain. Though 4.5 Å distance limit is preferred, one could also use longer distance limit (for example, 5.5 Å) in order to identify the interface residues (Bahar and Jernigan 1997).

The second method involves calculating solvent accessible surface area (ASA) of the CH3 domain residues in the presence and absence of the second chain (Lee and Richards 1971). The residues that show difference (>1 Å$^2$) in ASA between the two calculations are identified as interface residues. Both the methods identified similar set of interface residues. Further, they were consistent with the published work (Miller 1990).

Table 1 lists twenty four interface residues identified based on the contact criterion method, using the distance limit of 4.5 Å. These residues were further examined for structural conservation. For this purpose, 48 Fc crystal structures identified from the PDB were superimposed and analyzed by calculating root mean square deviation for the side chain heavy atoms. The residue designations are based on the EU numbering scheme of Kabat, which also corresponds to the numbering in the Protein Data Bank (PDB).

Figure 3:
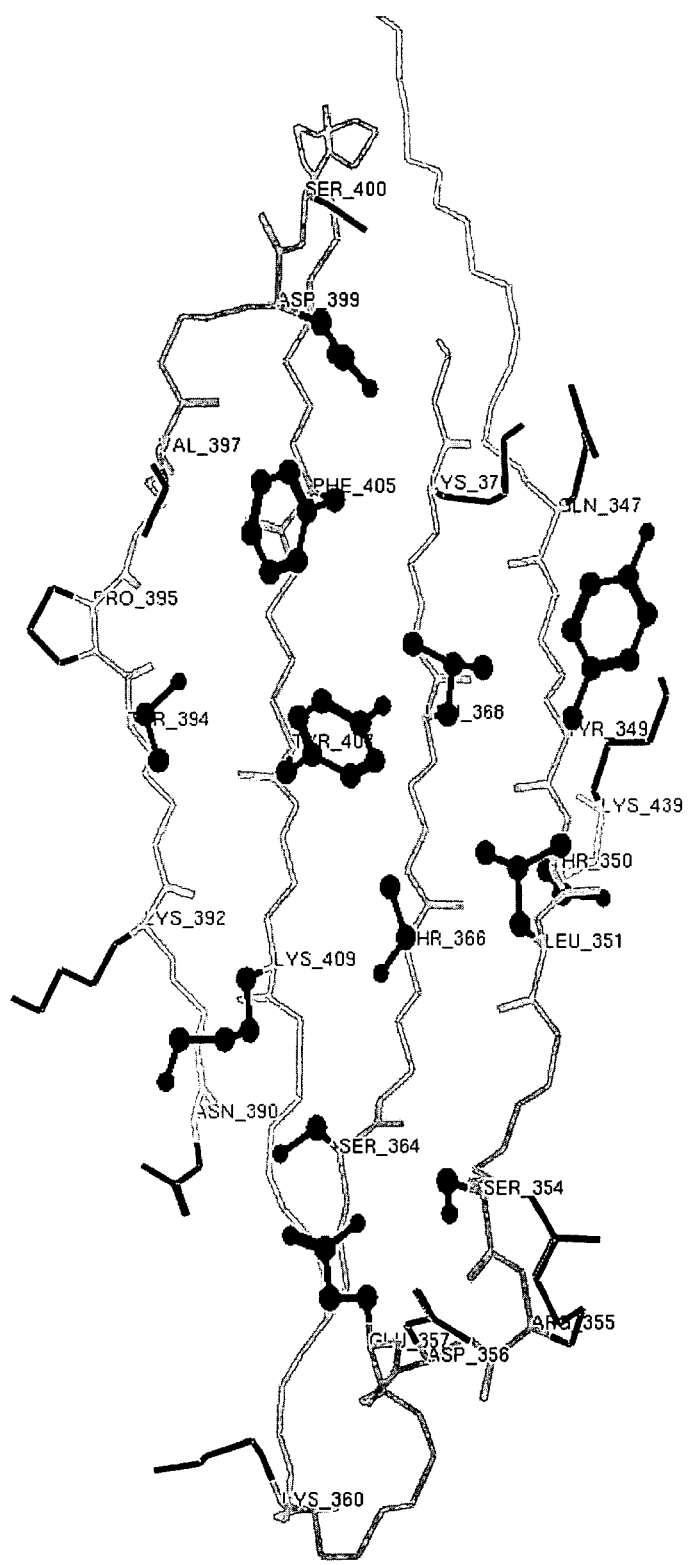
FIG. 3. CH3 domain interface structure with residues involved in the domain-domain interaction shown. The interface residues were identified using a distance cutoff method. Structurally conserved and buried (solvent accessible surface area <10%) residues are shown in the ball-and-stick model.

FIG. 3 shows the CH3 domain interface along with the structurally conserved, buried (% ASA≤10), and exposed (% ASA>10) positions (% ASA refers to ratio of observed ASA to the standard ASA of amino acids; (Lee and Richards 1971)). Conservation of interface residues among Human and Mouse IgG subclasses as well as among other Ig classes was also examined through sequence comparisons (FIG. 4A-4B).

TABLE 1

List of CH3 domain interface residues in the first chain (A)
and their contacting residues in the second chain (B)[a]

| Interface Res. in Chain A | Contacting Residues in Chain B |
|---|---|
| GLN A 347 | LYS B 360' |
| TYR A 349 | SER B 354' ASP B 356' GLU B 357' LYS B 360' |
| THR A 350 | SER B 354' ARG B 355' |
| LEU A 351 | LEU B 351' PRO B 352' PRO B 353' SER B 354' THR B 366' |
| SER A 354 | TYR B 349' THR B 350' LEU B 351' |
| ARG A 355[b] | THR B 350' |
| ASP A 356 | TYR B 349' LYS B 439' |
| GLU A 357 | TYR B 349' LYS B 370' |
| *LYS A 360*[b] | GLN B 347' TYR B 349' |
| SER A 364 | LEU B 368' LYS B 370' |
| THR A 366 | LEU B 351' TYR B 407' |
| LEU A 368 | SER B 364' LYS B 409' |
| LYS A 370 | GLU B 357' SER B 364' |
| ASN A 390 | SER B 400' |
| LYS A 392 | LEU B 398' ASP B 399' SER B 400' PHE B 405' |
| THR A 394 | THR B 394' VAL B 397' PHE B 405' TYR B 407' |
| PRO A 395 | VAL B 397' |
| VAL A 397 | THR B 393' THR B 394' PRO B 395' |
| ASP A 399 | LYS B 392' LYS B 409' |
| SER A 400 | ASN B 390' LYS B 392' |
| PHE A 405 | LYS B 392' THR B 394' LYS B 409' |
| TYR A 407 | THR B 366' THR B 394' TYR B 407' SER B 408' LYS B 409' |
| LYS A 409 | LEU B 368' ASP B 399' PHE B 405' TYR B 407' |
| LYS A 439 | ASP B 356' |

[a]Positions involving interaction between oppositely charged residues are indicated in bold. Due to the 2-fold symmetry present in the CH3—CH3 domain interaction, each pair-wise interaction is represented twice in the structure (for example, Asp A 356 - - - Lys B 439' & Lys A 439 - - - Asp B 356'; FIG. 5)
[b]Arg355 and Lys360 positions (shown in italics) could also be used for enhancing electrostatic steering effects though they are not involved in interaction with oppositely charged residues.

At neutral pH (=7.0), Asp and Glu residues are negatively charged and Lys, Arg and His are positively charged. These charged residues can be used to promote heterodimer formation and at the same time hinder homodimers. Attractive interaction takes place between opposite charges and repulsive interaction occurs between like charges. The method presented here makes use of the attractive and repulsive interactions for promoting heterodimer and hindering homodimer, respectively, by carrying out site directed mutagenesis of charged interface residues.

Examination of the identified CH3 domain interface residues (Table 1) reveals four unique charge residue pairs involved in the domain-domain interaction (Asp356- - - Lys439', Glu357- - - second Lys370', Lys392- - - Asp399', Asp399- - - Lys409'; residue numbering in the chain is indicated by prime '). These charge pairs are not necessarily involved in charge-charge interaction in the crystal structure used here (1L6X), since crystal structure is an end product in the protein folding reaction pathway and it represents structure in the crystalline state. It is assumed here that in order to have electrostatic steering effects it is sufficient if the residues are close in space as defined by the distance limit criterion (4.5 Å). It must also be noted here that due to the 2-fold symmetry present in the CH3-CH3 domain interaction, each unique interaction will be represented twice in the structure (for example, Asp399- - - Lys409' & Lys409- - - Asp399'; FIG. 5).

The four pairs were ranked according to the extent of solvent accessibility (ASA analysis) (Lee and Richards 1971). In Lys409- - - Asp399' case, both the residues were structurally conserved as well as buried. In other three pairs case, at least one of the partner is solvent exposed (% ASA>10). Therefore, for the Example herein, the Lys409- - - Asp399' pair was chosen for site directed mutagenesis. The strategy is schematically shown in FIG. 6.

In the wild type, K409- - - D399' interaction favors both heterodimer and homodimer formation. A single mutation switching the charge polarity (K409E; positive to negative charge) in the first chain leads to unfavorable interactions for the formation of the first chain homodimer. The unfavorable interactions arise due to the repulsive interactions occurring between the same charges (negative - - - negative; D399- - - K409E & K409E - - - D399). A similar mutation switching the charge polarity (D399'K; negative to positive charge) in the second chain leads to unfavorable interactions (K409' - - - D399'K & D399'K - - - K409') for the second chain homodimer formation. But, at the same time, these two mutations (K409E & D399'K) lead to favorable interactions (K409E - - - D399'K & D399- - - K409') for the heterodimer formation.

The electrostatic steering effects on heterodimer formation and homodimer discouragement can be further enhanced by mutation of additional charge residues which may or may not be paired with an oppositely charged residue in the second chain, such as Arg355 and Lys360, as shown in FIG. 6. The mutations shown in FIG. 6 are for the purpose of illustration only. Table 2 lists many possible mutations involving charge change, and the mutations can be combined to enhance the electrostatic effects.

Table 2a: List of some possible pair-wise charge residue mutations to enhance heterodimer formation[a]

| Position in the First Chain | Mutation in the First Chain | Interacting Position in the Second Chain | Corresponding Mutation in the Second Chain |
|---|---|---|---|
| Lys409 | Asp or Glu | Asp399' | Lys or Arg[b] |
| Lys392 | Asp or Glu | Asp399' | Lys or Arg[b] |
| Lys439 | Asp or Glu | Asp356' | Lys or Arg[b] |
| Lys370 | Asp or Glu | Glu357' | Lys or Arg[b] |
| Asp399 | Lys or Arg[b] | Lys409' | Asp or Glu |
| Asp399 | Lys or Arg[b] | Lys392' | Asp or Glu |
| Asp356 | Lys or Arg[b] | Lys439' | Asp or Glu |
| Glu357 | Lys or Arg[b] | Lys370' | Asp or Glu |

[a]Combinations of the above pair-wise charge residue mutations could also be used. For example Lys409 - - - Asp399' interaction pair mutations could be combined with Lys439 - - - Asp356' pair mutations.
[b]Histidine (His) could also be added to this list of positively charged residues, however, increase in side chain volume and pH dependency should be taken into account in the design.

Table 2b: Additional single charge residue mutations to enhance electrostatic steering effects[a]

| Position in Chain 1 | Mutation | Position in Chain 2 | Mutation |
|---|---|---|---|
| Arg355 | Asp or Glu | Arg355' | Asp or Glu |
| Lys360 | Asp or Glu | Lys360' | Asp or Glu |

[a]These single residue mutations could be combined with the Table 2a pair-wise mutations to enhance the heterodimer formation (FIG. 6).

Each positively charged residue (Lys and Arg) can be mutated to two negatively charged residues (Asp or Glu) and vice versa, and as a result the method described here provides numerous combinations. It must be stated here that different combinations will have diverse effect on the quaternary (homodimer/heterodimer) structure formation depending on surrounding residues at the mutation site and role of water molecules. The amino acid Histidine (His) is positively charged at neutral pH and therefore mutation to His also contemplated. However, mutating negatively charged residues (Asp or Glu) to His will lead to increase in side chain volume which may cause steric issues. Further, Histidine proton donor- and acceptor-form depends on the localized environment. These issues should be taken into consideration during the design strategy.

Because the interface residues are highly conserved in Human and Mouse IgG subclasses, electrostatic steering effects can be applied to Human or Mouse IgG1, IgG2, IgG3, or IgG4. This strategy can also be extended to modifying uncharged residues to charged residues at the CH3 domain interface. A similar strategy involving charge residue mutations can also be used to enhance homodimers and hinder heterodimer formation when two different heavy chains are co-expressed (FIG. 7).

In order to assess the stability of the charge residue mutants, EGAD software was used to estimate the CH3-CH3 domain binding free energy. By optimizing parameters used in the calculation, Pokala and Handel could predict the effects of nearly 400 mutations on protein-protein complex formation within 1.0 kcal/mol error (Pokala and Handel 2005). EGAD was used to roughly compare the binding free energy of various mutations made at the CH3 domain interface.

Figure 1:
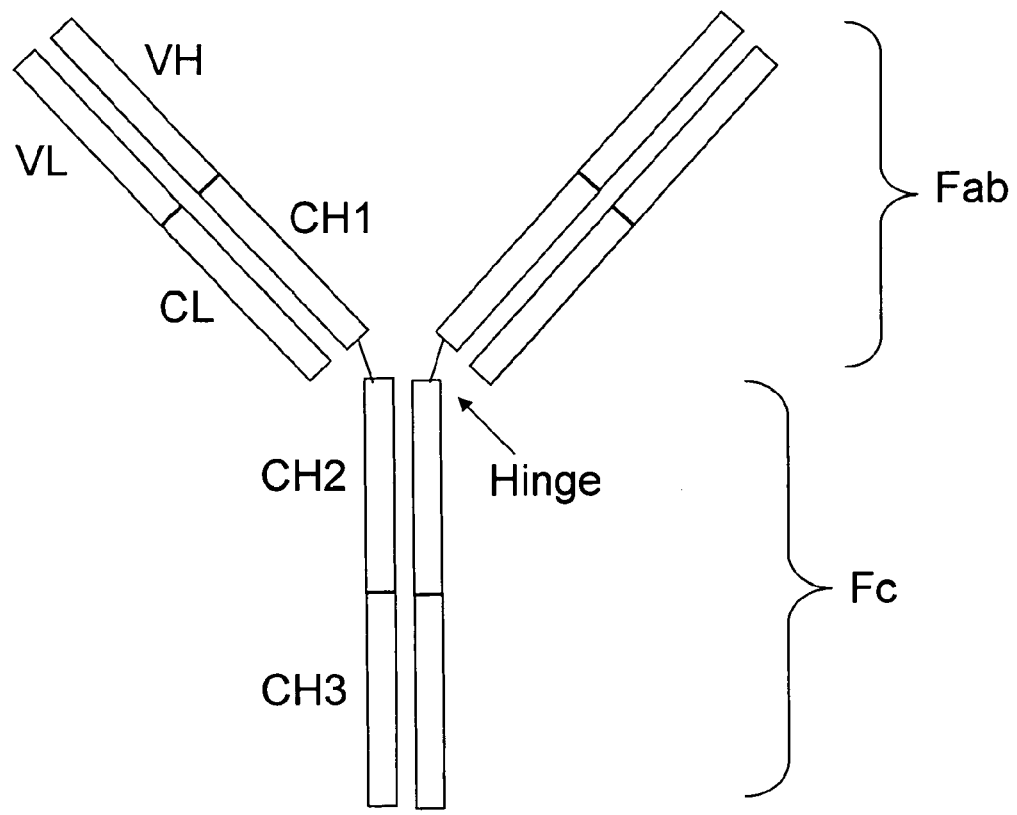
FIG. 1. Schematic diagram of IgG1 antibody with the domains indicated. The IgG1 antibody is a Y-shaped tetramer with two heavy chains (longer length) and two light chains (shorter length). The two heavy chains are linked together by disulfide bonds (—S—S—) at the hinge region. Fab—fragment antigen binding, Fc—fragment crystallizable, VL—variable light chain domain, VH—variable heavy chain domain, CL—constant (no sequence variation) light chain domain, CH1—constant heavy chain domain 1, CH2—constant heavy chain domain 2, CH3—constant heavy chain domain 3.
Figure 2:
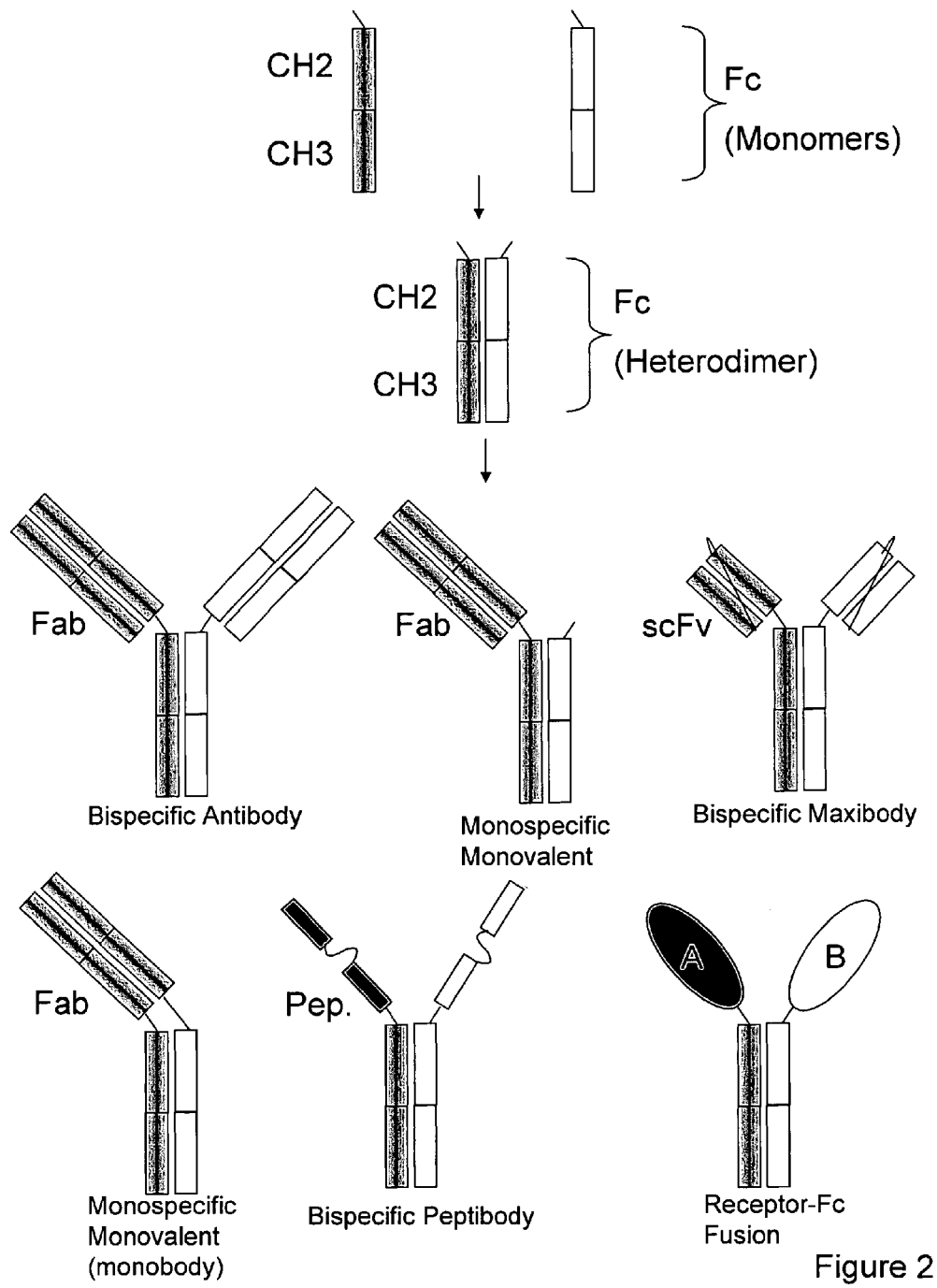
FIG. 2. Figure depicts some of the embodiments that include Fc-heterodimeric molecules. These include bispecific antibodies (have specificity for two or more antigens) to receptor-Fc fusion molecules. Preferably, the Fc retains its ability to interact with the FcRn receptor, even without the Fab domains, leading to longer serum half-life for proteins/domains that are fused to the Fc heavy chains. scFv—single chain fragment variable, Pep.—peptibody, A and B stands for proteins or receptors or domains.

Table 3 lists computed binding free energy ($\Delta\Delta G$) for the interface charge residue mutants. The binding free energy of a mutant is defined as $\Delta\Delta G_{mut}=\mu(\Delta G_{mut}-\Delta G_{wt})$. Where, $\mu(=0.1,$ in general) is the scaling factor used to normalize the predicted changes in binding affinity to have a slope of 1 when comparing with the experimental energies (Pokala and Handel 2005). The free energy of dissociation ($\Delta G$) is defined as the energy difference between the complex ($\Delta G_{bound}$) and free states ($\Delta G_{free}$). The comparison shows that charged residue mutations affect the stability to a much lesser extent compared to the knobs-into-holes mutations. For comparison, melting temperatures reported for the wild type and knobs-into-holes mutants are given. The melting temperatures were measured by Carter and coworkers using only the CH3 domain construct (Atwell, Ridgway et al. 1997). For the knobs-into-holes mutants, decrease in enthalpy was also observed in the differential scanning calorimetry experiments.

ing Fabs that bind to different antigens will lead to bispecifc antibodies (BsAbs). Fusing two different single-chain Fv (scFv; variable light and heavy chains joined by a flexible peptide linker) domains will lead to bispecific maxibodies. Further, domains or proteins that interact for functional reasons can also be fused with heterodimeric Fc for the purpose of developing functional assays or for therapeutic uses. For instance, in the hematopoietic receptor family gp130 is known to interact with other receptors such as Leukemia Inhibitory Factor Receptor (LIFR). The extra cellular domain (ECD) of gp130 can be fused to the first heavy chain of Fc and the ECD of LIFR can be fused to the second Fc heavy chain, which will lead to formation of gp130-LIFR complex that is likely to mimic the biological state. Since FcRn binding site is located in the Fc region, Fc fusion molecules are likely to have extended serum half-life—a feature that distinguishes Fc heterodimeric molecules from other heterodimeric molecules such as leucine zipper fusion proteins (Liu, Caderas et al. 2001). It is not essential to have different functionalities attached to the two heavy chains of the Fc heterodimer. A monobody can also be created (FIG. 2).

In certain embodiments, e.g., when producing bispecific antibodies, multiple different light chains may be co-expressed with the multiple different heavy chains. To increase the fidelity of each light chain binding to the proper heavy chain thereby maintaining specificity of the antibody "arm," the CH1 domains of one or more of the heavy chains and the constant region of one or more of the light chains can be engineered to favor dimerization. Preferably, this is accomplished using an electrostatic steering technique similar to that described above for the CH3 domains The interaction of the kappa light chain sequence corresponding to the Protein Data Bank (PDB) deposition code 1N0X (SEQ ID NO:25) and the lambda light chain corresponding to (PDB) deposition code 7FAB (SEQ ID NO:26) with the heavy chain sequence corresponding to the CH1 domain of IgG1 (SEQ ID NO:27) was analyzed. The lambda light chain-Heavy chain contacts within the interface are shown in Table 4.

TABLE 3

CH3—CH3 domain binding free energy for various mutants designed to enhance heterodimer formation, calculated using the EGAD program (Pokala and Handel 2005)[a]

| Protein | Description | $\Delta G$ (in kcal/mol) | $\Delta\Delta G_{mut}$ (in kcal/mol) | Melting Temp. $T_m$ (in ° C.) |
|---|---|---|---|---|
| WT | Wild Type | −30.69 | 0 | 80.4 |
| T366W-Y407'A | Knob-Hole | −24.60 | 6.09 | 65.4 |
| T366W-T366'S-L368'A-Y407'V | Knob-Hole | −28.57 | 2.12 | 69.4 |
| K409E-D399'K | Charge-Charge | −29.56 | 1.13 | ND |
| K409E-D399'R | Charge-Charge | −29.47 | 1.22 | ND |
| K409D-D399'K | Charge-Charge | −28.16 | 2.53 | ND |
| K409D-D399'R | Charge-Charge | −27.69 | 3.00 | ND |
| K392E-D399'R | Charge-Charge | −29.27 | 1.42 | ND |
| K392E-D399'K | Charge-Charge | −29.87 | 0.82 | ND |
| K392D-D399'R | Charge-Charge | −28.82 | 1.87 | ND |
| K392D-D399'R | Charge-Charge | −29.42 | 1.27 | ND |

[a]Not all possible charge-charge pairs were considered for the binding free energy calculation. Wild type is listed for comparison. $\Delta G$ is defined as energy difference between the complex and free states. The binding free energy of a mutant ($\Delta\Delta G_{mut}$) is defined as difference between the mutant ($\Delta G_{mut}$) and wild type ($\Delta G_{WT}$) free energies.

FIG. 2 depicts several embodiments comprising Fc heterodimeric molecules, from bispecific antibodies to heterodimeric receptor complexes. The two heavy chains of heterodimeric Fc molecules can be fused with proteins and/or domains that have different functionalities. For example, fus-

TABLE 4

List of lambda light chain interface residues and their contacting residues in the heavy chain[a]

| Interface Res. in Lambda Light Chain | Contacting Residues in the Heavy Chain |
|---|---|
| THR L 112 | ALA H 141 |
| PHE L 114 | LEU H 128 ALA H 129 ALA H 141 LEU H 142 GLY H 143 VAL H 185 |
| SER L 117 | PHE H 126 PRO H 127 |
| GLU L 119 | VAL H 125 PHE H 126 PRO H 127 LYS H 213 |
| GLU L 120 | PHE H 126 |
| LYS L 125 | LYS H 147 ASP H 148 |
| THR L 127 | LEU H 145 LYS H 147 |
| VAL L 129 | LEU H 128 LEU H 145 SER H 183 |
| LEU L 131 | PHE H 170 SER H 183 VAL H 185 |
| SER L 133 | HIS H 168 PHE H 170 |
| GLU L 156 | VAL H 173 LEU H 174 GLN H 175 SER H 176 |
| THR L 158 | PRO H 171 ALA H 172 VAL H 173 |
| SER L 161 | PRO H 171 |
| GLN L 163 | HIS H 168 |
| ALA L 169 | HIS H 168 PHE H 170 |
| SER L 171 | PHE H 170 PRO H 171 |
| TYR L 173 | LEU H 145 VAL H 173 SER H 181 LEU H 182 SER H 183 |

[a]Contacting residues were identified using 4.5 Å distance limit criterion. The light and heavy chain numbering scheme corresponds to that in the deposited co-ordinates file (PDB code: 7FAB).

The kappa light chain-heavy chain contacts within the interface are shown in Table 5.

TABLE 5

List of kappa light chain interface residues and their contacting residues in the heavy chain[a]

| Interface Res. in Kappa Light Chain | Contacting Residues in the Heavy Chain |
|---|---|
| PHE 116 | THR H 139 ALA H 140 ALA H 141 |
| PHE 118 | LEU H 128 ALA H 129 PRO H 130 ALA H 141 LEU H 142 |
| SER 121 | PHE H 126 PRO H 127 |
| ASP 122 | LYS H 218 |
| GLU 123 | VAL H 125 PHE H 126 LYS H 213 |
| GLN 124 | PHE H 126 LEU H 145 LYS H 147 |
| SER 131 | LEU H 145 LYS H 147 |
| VAL 133 | LEU H 128 |
| LEU 135 | ALA H 141 PHE H 170 VAL H 185 |
| ASN 137 | HIS H 168 THR H 187 |
| ASN 138 | HIS H 168 |
| GLN 160 | VAL H 173 LEU H 174 GLN H 175 |
| SER 162 | PHE H 170 PRO H 171 VAL H 173 |
| THR 164 | THR H 169 PHE H 170 PRO H 171 |
| SER 174 | HIS H 168 PHE H 170 |
| SER 176 | PHE H 170 SER H 183 |

[a]Contacting residues were identified using 4.5 Å distance limit criterion. The light chain numbering scheme corresponds to that in the deposited co-ordinates file (PDB code: 1N0X). The heavy chain numbering scheme corresponds to that in the Table 4.

In certain embodiments, Lys 125 of the lambda chain is mutated to a negatively charged amino acid and a corresponding mutation is made in a heavy chain at Asp148, changing the residue to a positively charged amino acid. Alternatively, or in addition, Glu119 of the lambda chain is mutated to a positively charged amino acid a corresponding mutation is made in a heavy chain at Lys213, changing the residue to a negatively charged amino acid.

The analysis of the light chain-heavy chain interaction revealed positions in which charge pairs could be introduced into the sequence to enhance binding of a specific light and heavy chain pair. These positions include Thr112 of lambda and Ala141 of the heavy chain, Glu 156 of lambda and Ser176 of the heavy chain, and Ser171 of lambda and Ser183 of the heavy chain and other positions shown in Table 4 and 5 in bold face.

EXAMPLES

Example 1

This example demonstrates that CH3 domains can be engineered to favor heterodimerization while disfavoring homodimerization using electrostatic steering effects. A maxibody—dummy Fc construct as shown in FIG. 8(a) was made having charge residue mutations at the CH3 domain interface. The formation of homodimer and heterodimer yield was assessed through SDS polyacrylamide gel electrophoresis. Because the maxibody has a higher molecular weight compared to dummy Fc, the heterodimer (maxibody-dummy Fc) and homodimers (maxibody-maxibody & dummy Fc-dummy Fc) have different mobility on the SDS-PAGE facilitating the identification of the various pairings (FIG. 8(b)).

A rat anti-mouse NKG2D antibody, designated M315, was generated through conventional hybridoma fusions and the DNA sequences encoding the variable heavy chain (VH) and variable light chain (VL) were used to construct M315 scFv-Fc using previously described method (Gilliland, Norris, et al. 1996).

The sequence of M315 scFv-Fc (SEQ ID NO:1) and huIgG1 Fc (SEQ ID NO:2) were cloned into the pTT5 mammalian expression vector and the two constructs were used to co-transfect 293-6E cells to assess the formation Fc/scFv-Fc heterodimer relative to Fc homodimer and scFv-Fc homodimer.

```
M315scFv-huFc
                                                SEQ ID NO: 1
HMAEVQLQQSGAELVKPGSSVISCKASGYTFANNFMHWIKQQPGNGLEW

IGWIYPGDGDTEYNQKFSGKATLTADKSSSTAYMQLNSLTSEDSAVYFCI

RLTEGTTYWGQGVMVTVSSGGGGSGGGGSGGGGSQFVLTQPNSVSTNLGS

TVKLSCKRSTGNIGSNYVMWYQQHEGRSPTTMIYRDDKRPDGVPDRFSGS

IDGSSNSALLTINNVQTEDEADYFCQSYSRGVSPVFGGGTKLTVLAAAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK huIgG1-Fc
                                                SEQ ID NO: 2
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDK

SRWQQGNVFSCSVMHEALHNHYTQKSLSLSPGK
```
(Shading corresponds to the Fc region)

The charge residue pairs in the CH3 region identified through computational analysis were changed to amino acid of opposite charge polarity on either human IgG1Fc (dummy) or M315 scFv-Fc (mxb) constructs. The mutations, which are listed in Table 6, were generated using the QuikChange® mutagenesis kit from Stratagene and verified by DNA sequencing. The mutations are denoted by wild type residue followed by the position using the Kabat numbering system (Kabat et al., *Sequences of Proteins of Immunological Interest*, National Institutes of Health, Bethesda, Md., ed, 5, [1991]), which is consistent with the crystal structure (PDB code: 1L6X) numbering scheme, and then the replacement residue in single letter code. The Fc sequence used in these two constructs was derived from human IgG1 non-(a) allotype, which has a Glu at position 356 and a Met at position 358. The CH3 sequences from the crystal structure are from a different IgG1 allotype, which has an Asp at position 356 and a Leu at position 368.

TABLE 6

List of charge residue mutations

| huIgG1Fc (dummy) | M315 scFv-Fc(mxb) |
|---|---|
| Fc-WT | M315 scFv-Fc(WT) |
| K409D | D399'K |
| K409E | D399'R |
| K409D&K360D | D399'K&E356'K |
| K409D&K370D | D399'K&E357'K |
| K409D&K392D | D399'K&E356'K&E357'K |
| K409D&K439D | |

DNA was transfected into human embryonic kidney cell line 293-6E using Lipofectamine™ 2000 reagent (Invitrogen). The cell culture supernatant was harvested 3-4 days after transfection and analyzed on SDS-PAGE Gels under non-reduced condition. The gel was then transferred to nitrocellulose membrane and subject to western analysis using peroxidase-conjugated goat anti-human IgG antibody (Jackson ImmunoResearch Laboratories) and results are shown in FIG. 10.

Co-transfection of expression vector for M315 scFv-Fc (mxb) together with dummy Fc resulted in the formation of scFv-Fc/Fc heterodimer as well as scFv-Fc homodimer and Fc homodimer. The ratio of scFv-Fc/Fc heterodimer to scfv-Fc homodimer and Fc homodimer is close to 1:1:1 when the wild type CH3 sequence is used.

The introduction of one charge pair mutation K409D on dummy Fc and D399'K on M315 maxibody significantly increased the ratio of scFv-Fc/Fc heterodimer relative to scFv-Fc homodimer as well as Fc homodimer. Similar enhancement of heterodimer formation was also observed for other mutant variants such as K409D/D399'R, K409E/D399'K and K409E/D399'R (FIG. 9), further underscore the importance of charge polarity complementation for the formation of Fc heterodimers. (The wild type M315 scFv-Fc construct used in this study has an extra tag at the carboxyl terminal of Fc, so it migrates slower on the SDS-PAGE gel.)

When additional mutations were introduced at charge residues that are located near K409 such as K360 and K392, a further increase of heterodimer formation was observed (FIG. 10). For example, the combination K409D; K392D on dummy Fc with D399'K on M315 maxibody showed increased ratio of heterodimer to homodimers, likely due to the disruption of Fc homodimer. A 25 KD band correspond to the size of Fc monomer was detected on all transfections using K409D; K392D dummy Fc (data not shown). Adding another mutation such as D356'K or D357'K on top of D399'K variant of M315 maxibody showed additional improvement. The combination of K409D; K392D on dummy Fc with D399'K; D356'K on M315 maxibody resulted almost exclusive formation of heterodimer. Other combinations such as K409D; K392D/D399'K; D357'K and K409D; K370D/D399'K; D357'K also offered significant improvement over the K409D/D399'K variant.

Example 2

This example demonstrates that CH3 domains containing certain triple charge-pair mutations were unable to form homodimers when expressed alone but were capable of forming heterodimers when co-expressed. Mutants were made and cells transfected as described in Example 1. When the constructs were co-transfected, a 1:1 ratio of plasmids were used. The results are shown in FIG. 11. Heterodimer and homodimers were detected by Western blot using goat-anti-human Fc HRP conjugated antibody. Interestingly, Fc-containing molecules having triple mutations wherein positive-charged residues were changed to negative-charged residues (K409D, K392D, K370D or K409D, K392D, K439D) were unable to be detected when expressed alone. Similarly, Fc-containing molecules having triple mutations wherein negative-charged residues were changed to positive-charged residues (D399K, E356K, E357K) were unable to be detected when expressed alone. When co-expressed with an Fc-containing molecule having mutations of opposite charge polarity, however, heterodimers only were detected.

Throughout this invention application, it is to be understood that use of a term in the singular may imply, where appropriate, use of respective term in the plural, and vice versa.

Atwell, S., J. B. Ridgway, et al. (1997). "Stable heterodimers from remodeling the domain interface of a homodimer using a phage display library." *J Mol Biol* 270(1): 26-35.

Bahar, I. and R. L. Jernigan (1997). "Inter-residue potentials in globular proteins and the dominance of highly specific hydrophilic interactions at close separation." *J Mol Biol* 266(1): 195-214.

Bernstein, F. C., T. F. Koetzle, et al. (1977). "The Protein Data Bank: a computer-based archival file for macromolecular structures." *J Mol Biol* 112(3): 535-42.

Bogan, A. A. and K. S. Thorn (1998). "Anatomy of hot spots in protein interfaces." *J Mol Biol* 280(1): 1-9.

Carter, P. (2001). "Bispecific human IgG by design." *J Immunol Methods* 248(1-2): 7-15.

Crick, F. H. (1952). "Is alpha-keratin a coiled coil?" *Nature* 170(4334): 882-3.

de Leij, L., G. Molema, et al. (1998). "Bispecific antibodies for treatment of cancer in experimental animal models and man." *Adv Drug Deliv Rev* 31(1-2): 105-129.

Deisenhofer, J. (1981). "Crystallographic refinement and atomic models of a human Fc fragment and its complex

TABLE 7

Quantification of percentage of homodimer and heterodimer yields for the SDS-PAGE shown in FIG. 10.[a]

| Dummy Fc Homodimer | M315 scFv-Fc - Dummy Fc Heterodimer | M315 scFv-Fc Homodimer | M315 scFv-Fc | Dummy Fc |
|---|---|---|---|---|
| 42.1 | 32.4 | 25.5 | WT | WT |
| 28.1 | 55.1 | 16.8 | D399'K | K409D; K360D |
| ND | 76.9 | 23.1 | D399'K | K409D; K392D |
| ND | 100 | ND | D399'K; E356'K | K409D; K392D |
| 20.9 | 79.1 | ND | D399'K; E357'K | K409D; K392D |
| 7.7 | 92.3 | ND | D399'K; E356'K | K409D; K439D |
| 14.8 | 85.2 | ND | D399'K; E357'K | K409D; K370D |
| ND | 86.7 | 13.3 | T366'W (Hole) | T366S; L368A; Y407V (Knob) |

[a]ND stands for Not Detectable in the density based analysis.

with fragment B of protein A from *Staphylococcus aureus* at 2.9- and 2.8-A resolution." *Biochemistry* 20(9): 2361-70.

Gabdoulline, R. R. and R. C. Wade (2002). "Biomolecular diffusional association." *Curr Opin Struct Biol* 12(2): 204-13.

Ghetie, V. and E. S. Ward (2000). "Multiple roles for the major histocompatibility complex class I-related receptor FcRn." *Annu Rev Immunol* 18: 739-66.

Gilliland, L. K., N. A. Norris, et al. (1996). "Rapid and reliable cloning of antibody variable regions and generation of recombinant single chain antibody fragments." *Tissue Antigens* 47(1): 1-20

Halperin, I., H. Wolfson, et al. (2004). "Protein-protein interactions; coupling of structurally conserved residues and of hot spots across interfaces. Implications for docking." *Structure* 12(6): 1027-38.

Huber, R. (1984). "Three-dimensional structure of antibodies." *Behring Inst Mitt*(76): 1-14.

Idusogie, E. E., L. G. Presta, et al. (2000). "Mapping of the C1q binding site on rituxan, a chimeric antibody with a human IgG1Fc." *J Immunol* 164(8): 4178-84.

Joachimiak, L. A., T. Kortemme, et al. (2006). "Computational design of a new hydrogen bond network and at least a 300-fold specificity switch at a protein-protein interface." *J Mol Biol* 361(1): 195-208.

King, D. J., J. R. Adair, et al. (1992). "Expression, purification and characterization of a mouse-human chimeric antibody and chimeric Fab' fragment." *Biochem J* 281 (Pt 2): 317-23.

Kortemme, T. and D. Baker (2004). "Computational design of protein-protein interactions." *Curr Opin Chem Biol* 8(1): 91-7.

Kortemme, T., L. A. Joachimiak, et al. (2004). "Computational redesign of protein-protein interaction specificity." *Nat Struct Mol Biol* 11(4): 371-9.

Laemmli, U. K. (1970). "Cleavage of structural proteins during the assembly of the head of bacteriophage T4." *Nature* 227(5259): 680-5.

Lee, B. and F. M. Richards (1971). "The interpretation of protein structures: estimation of static accessibility." *J Mol Biol* 55(3): 379-400.

Liu, N., G. Caderas, et al. (2001). "Fusion proteins from artificial and natural structural modules." *Curr Protein Pept Sci* 2(2): 107-21.

Maizel, J. V., Jr., D. F. Summers, et al. (1970). "SDS-acrylamide gel electrophoresis and its application to the proteins of poliovirus- and adenovirus-infected human cells." *J Cell Physiol* 76(3): 273-87.

Martin, W. L., A. P. West, Jr., et al. (2001). "Crystal structure at 2.8 A of an FcRn/heterodimeric Fc complex: mechanism of pH-dependent binding." *Mol Cell* 7(4): 867-77.

Marvin, J. S, and H. B. Lowman (2003). "Redesigning an antibody fragment for faster association with its antigen." *Biochemistry* 42(23): 7077-83.

Matthews, B. W. (1995). "Studies on protein stability with T4 lysozyme." *Adv Protein Chem* 46: 249-78.

Merchant, A. M., Z. Zhu, et al. (1998). "An efficient route to human bispecific IgG." *Nat Biotechnol* 16(7): 677-81.

Miller, S. (1990). "Protein-protein recognition and the association of immunoglobulin constant domains." *J Mol Biol* 216(4): 965-73.

Nolan, O. and R. O'Kennedy (1990). "Bifunctional antibodies: concept, production and applications." *Biochim Biophys Acta* 1040(1): 1-11.

Papadea, C. and I. J. Check (1989). "Human immunoglobulin G and immunoglobulin G subclasses: biochemical, genetic, and clinical aspects." *Crit. Rev Clin Lab Sci* 27(1): 27-58.

Pokala, N. and T. M. Handel (2005). "Energy functions for protein design: adjustment with protein-protein complex affinities, models for the unfolded state, and negative design of solubility and specificity." *J Mol Biol* 347(1): 203-27.

Raghavan, M. and P. J. Bjorkman (1996). "Fc receptors and their interactions with immunoglobulins." *Annu Rev Cell Dev Biol* 12: 181-220.

Ridgway, J. B., L. G. Presta, et al. (1996). "'Knobs-into-holes' engineering of antibody CH3 domains for heavy chain heterodimerization." *Protein Eng* 9(7): 617-21.

Roux, K. H. (1999). "Immunoglobulin structure and function as revealed by electron microscopy." *Int Arch Allergy Immunol* 120(2): 85-99.

Schreiber, G., Y. Shaul, et al. (2006). "Electrostatic design of protein-protein association rates." *Methods Mol Biol* 340: 235-49.

Selzer, T., S. Albeck, et al. (2000). "Rational design of faster associating and tighter binding protein complexes." *Nat Struct Biol* 7(7): 537-41.

Sheinerman, F. B., R. Norel, et al. (2000). "Electrostatic aspects of protein-protein interactions." *Curr Opin Struct Biol* 10(2): 153-9.

Sondermann, P., R. Huber, et al. (2000). "The 3.2-A crystal structure of the human IgG1Fc fragment-Fc gammaRIII complex." *Nature* 406(6793): 267-73.

Sowdhamini, R., N. Srinivasan, et al. (1989). "Stereochemical modeling of disulfide bridges. Criteria for introduction into proteins by site-directed mutagenesis." *Protein Eng* 3(2): 95-103.

Szczepek, M., V. Brondani, et al. (2007). "Structure-based redesign of the dimerization interface reduces the toxicity of zinc-finger nucleases." *Nat Biotechnol* 25(7): 786-93.

Ye, Y. and A. Godzik (2004). "FATCAT: a web server for flexible structure comparison and structure similarity searching." *Nucleic Acids Res* 32(Web Server issue): W582-5.

The invention claimed is:

1. An isolated heterodimeric protein comprising a first human CH3-containing polypeptide and a second human IgG CH3-containing polypeptide wherein said first human CH3-containing polypeptide comprises a replacement of the amino acid at position 392 with a negative-charged amino acid and said second human IgG CH3-containing polypeptide comprises a replacement of Asp399, Glu356, Asp356, or Glu357 with a positive-charged amino acid.

2. The isolated heterodimeric protein of claim 1, wherein Lys392 is replaced with a negative-charged amino acid.

3. The isolated heterodimeric protein of claim 2, wherein Asn392 is replaced with a negative-charged amino acid.

4. The isolated heterodimeric protein of claim 1, wherein said first human CH3-containing polypeptide further comprises Lys409 or Arg409 replaced with a negative-charged amino acid.

5. The isolated heterodimeric protein of claim 4, wherein said first human CH3-containing polypeptide wherein Lys392 or Asn392 is replaced with aspartic acid.

6. The isolated heterodimeric protein of claim 5, wherein said Lys409 or Arg409 is replaced with aspartic acid.

7. The isolated heterodimeric protein of claim 6, wherein said second human IgG CH3-containing polypeptide comprises a replacement of Asp399, Glu356, Asp356, or Glu357 with lysine.

8. The isolated heterodimeric protein of claim 7, wherein said second human IgG CH3-containing polypeptide comprises a replacement of Asp399 and Glu356 with lysine.

9. The isolated heterodimeric protein of claim 1, wherein the heterodimeric protein comprises a human IgG Fc region.

10. The isolated heterodimeric protein of claim 9, wherein the human IgG Fc region comprises an IgG1 Fc region.

11. The isolated heterodimeric protein of claim 9, wherein the IgG Fc region comprises an IgG2 Fc region.

12. The isolated heterodimeric protein of claim 9, wherein the IgG Fc region comprises an IgG3 Fc region.

13. The isolated heterodimeric protein of claim 9, wherein the IgG Fc region comprises an IgG4 Fc region.

14. The isolated heterodimeric protein of claim 1, wherein the first CH3-containing polypeptide is an antibody heavy chain.

15. The isolated heterodimeric protein of claim 1, wherein the second CH3-containing polypeptide is an antibody heavy chain.

16. The isolated heterodimeric protein of claim 1, wherein the heterodimeric protein further comprises one or more antibody light chains.

17. The isolated heterodimeric protein of claim 1, wherein the heterodimeric protein is selected from the group consisting of an antibody, a bispecific antibody, a monospecific monovalent antibody, a bispecific maxibody, a monobody, a peptibody, a bispecific peptibody, a monovalent peptibody, and a receptor fusion protein.

18. A pharmaceutical composition comprising a heterodimeric protein of claim 1.

* * * * *

SEQUENCE LISTING

```
<160> NUMBER OF SEQ ID NOS: 24

<210> SEQ ID NO 1
<211> LENGTH: 480
<212> TYPE: PRT
<213> ORGANISM: M315scFv-huFc

<400> SEQUENCE: 1
```

```
His Met Ala Glu Val Gln Leu Gln Gln Ser Gly Ala Glu Leu Val Lys
1               5                   10                  15

Pro Gly Ser Ser Val Lys Ile Ser Cys Lys Ala Ser Gly Tyr Thr Phe
            20                  25                  30

Ala Asn Asn Phe Met His Trp Ile Lys Gln Gln Pro Gly Asn Gly Leu
        35                  40                  45

Glu Trp Ile Gly Trp Ile Tyr Pro Gly Asp Gly Asp Thr Glu Tyr Asn
    50                  55                  60

Gln Lys Phe Ser Gly Lys Ala Thr Leu Thr Ala Asp Lys Ser Ser Ser
65                  70                  75                  80

Thr Ala Tyr Met Gln Leu Asn Ser Leu Thr Ser Glu Asp Ser Ala Val
                85                  90                  95

Tyr Phe Cys Ile Arg Leu Thr Glu Gly Thr Thr Tyr Trp Gly Gln Gly
            100                 105                 110

Val Met Val Thr Val Ser Ser Gly Gly Gly Ser Gly Gly Gly Gly
            115                 120                 125

Ser Gly Gly Gly Gly Ser Gln Phe Val Leu Thr Gln Pro Asn Ser Val
    130                 135                 140

Ser Thr Asn Leu Gly Ser Thr Val Lys Leu Ser Cys Lys Arg Ser Thr
145                 150                 155                 160

Gly Asn Ile Gly Ser Asn Tyr Val Asn Trp Tyr Gln Gln His Glu Gly
            165                 170                 175

Arg Ser Pro Thr Thr Met Ile Tyr Arg Asp Asp Lys Arg Pro Asp Gly
            180                 185                 190

Val Pro Asp Arg Phe Ser Gly Ser Ile Asp Gly Ser Ser Asn Ser Ala
    195                 200                 205

Leu Leu Thr Ile Asn Asn Val Gln Thr Glu Asp Glu Ala Asp Tyr Phe
210                 215                 220

Cys Gln Ser Tyr Ser Arg Gly Val Ser Pro Val Phe Gly Gly Gly Thr
225                 230                 235                 240

Lys Leu Thr Val Leu Ala Ala Ala Glu Pro Lys Ser Cys Asp Lys Thr
            245                 250                 255

His Thr Cys Pro Pro Cys Pro Ala Pro Glu Leu Leu Gly Gly Pro Ser
        260                 265                 270

Val Phe Leu Phe Pro Pro Lys Pro Lys Asp Thr Leu Met Ile Ser Arg
    275                 280                 285

Thr Pro Glu Val Thr Cys Val Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
            325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Ser Arg Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
            405                 410                 415

Asn Gly Gln Pro Glu Asn Asn Tyr Lys Thr Thr Pro Pro Val Leu Asp
            420                 425                 430
```

```
Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
        450                 455                 460

Leu His Asn His Tyr Thr Gln Lys Ser Leu Ser Leu Ser Pro Gly Lys
465                 470                 475                 480

<210> SEQ ID NO 2
<211> LENGTH: 232
<212> TYPE: PRT
<213> ORGANISM: Human IgG1-Fc

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 326
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95
```

```
Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 5
<211> LENGTH: 377
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
130                 135                 140
```

```
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
            165                 170                 175

Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 6
<211> LENGTH: 327
<212> TYPE: PRT
<213> ORGANISM: homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 353
<212> TYPE: PRT
<213> ORGANISM: Homo sapiens

<400> SEQUENCE: 7

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190
```

```
Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 8
<211> LENGTH: 384
<212> TYPE: PRT
<213> ORGANISM: Homo sapiens

<400> SEQUENCE: 8

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205
```

```
Lys Val Pro Thr Gly Gly Val Glu Glu Gly Leu Leu Glu Arg His Ser
            210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380

<210> SEQ ID NO 9
<211> LENGTH: 428
<212> TYPE: PRT
<213> ORGANISM: Homo sapains

<400> SEQUENCE: 9

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro
        115                 120                 125

Pro Thr Ile Gln Leu Leu Cys Leu Val Ser Gly Tyr Thr Pro Gly Thr
            130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205
```

```
Cys Ala Asp Ser Asn Pro Arg Gly Val Ser Ala Tyr Leu Ser Arg Pro
            210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
355                 360                 365

Ala Arg His Ser Thr Thr Gln Pro Arg Lys Thr Lys Gly Ser Gly Phe
        370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425

<210> SEQ ID NO 10
<211> LENGTH: 452
<212> TYPE: PRT
<213> ORGANISM: Homo sapiens

<400> SEQUENCE: 10

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160
```

```
Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450

<210> SEQ ID NO 11
<211> LENGTH: 109
<212> TYPE: PRT
<213> ORGANISM: Human IgG1

<400> SEQUENCE: 11

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80
```

```
Gln Gly Asn Val Phe Ser Cys Ser Val Met His Glu Ala Leu His Asn
            85                  90                  95

His Tyr Thr Gln Lys Ser Leu Ser Leu Ser Pro Gly Lys
            100                 105

<210> SEQ ID NO 12
<211> LENGTH: 109
<212> TYPE: PRT
<213> ORGANISM: Human IgG2

<400> SEQUENCE: 12

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Met Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
            85                  90                  95

His Tyr Thr Gln Lys Ser Leu Ser Leu Ser Pro Gly Lys
            100                 105

<210> SEQ ID NO 13
<211> LENGTH: 109
<212> TYPE: PRT
<213> ORGANISM: Human IgG3

<400> SEQUENCE: 13

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Ser Gly Gln
        35                  40                  45

Pro Glu Asn Asn Tyr Asn Thr Thr Pro Pro Met Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Ile Phe Ser Cys Ser Val Met His Glu Ala Leu His Asn
            85                  90                  95

Arg Phe Thr Gln Lys Ser Leu Ser Leu Ser Pro Gly Lys
            100                 105

<210> SEQ ID NO 14
<211> LENGTH: 109
<212> TYPE: PRT
<213> ORGANISM: Human IgG4

<400> SEQUENCE: 14

Ala Lys Gly Gln Pro Arg Glu Pro Gln Val Tyr Thr Leu Pro Pro Ser
1               5                   10                  15

Gln Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45
```

```
Pro Glu Asn Asn Tyr Lys Thr Thr Pro Pro Val Leu Asp Ser Asp Gly
    50                  55                  60

Ser Phe Phe Leu Tyr Ser Arg Leu Thr Val Asp Lys Ser Arg Trp Gln
65                  70                  75                  80

Glu Gly Asn Val Phe Ser Cys Ser Val Met His Glu Ala Leu His Asn
                85                  90                  95

His Tyr Thr Gln Lys Ser Leu Ser Leu Ser Leu Gly Lys
            100                 105

<210> SEQ ID NO 15
<211> LENGTH: 106
<212> TYPE: PRT
<213> ORGANISM: Human IgG1

<400> SEQUENCE: 15

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
                20                  25                  30

Gly Phe Tyr Pro Ser Asp Ile Ala Val Glu Trp Glu Ser Asn Gly Gln
            35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser
            100                 105

<210> SEQ ID NO 16
<211> LENGTH: 106
<212> TYPE: PRT
<213> ORGANISM: Mouse IgG1

<400> SEQUENCE: 16

Thr Lys Gly Arg Pro Lys Ala Pro Gln Val Tyr Thr Ile Pro Pro Pro
1               5                   10                  15

Lys Glu Gln Met Ala Lys Asp Lys Val Ser Leu Thr Cys Met Ile Thr
                20                  25                  30

Asp Phe Phe Pro Glu Asp Ile Thr Val Glu Trp Gln Trp Asn Gly Gln
            35                  40                  45

Pro Ala Glu Asn Tyr Lys Asn Thr Gln Pro Ile Met Asn Thr Asn Gly
    50                  55                  60

Ser Tyr Phe Val Tyr Ser Lys Leu Asn Val Gln Lys Ser Asn Trp Glu
65                  70                  75                  80

Ala Gly Asn Thr Phe Thr Cys Ser Val Leu His Glu Gly Leu His Asn
                85                  90                  95

His His Thr Glu Lys Ser Leu Ser His Ser
            100                 105

<210> SEQ ID NO 17
<211> LENGTH: 106
<212> TYPE: PRT
<213> ORGANISM: Mouse IgG2a

<400> SEQUENCE: 17
```

Pro Lys Gly Ser Val Arg Ala Pro Gln Val Tyr Val Leu Pro Pro
1               5                   10                  15

Glu Glu Glu Met Thr Lys Lys Gln Val Thr Leu Thr Cys Met Val
                20                  25                  30

Asp Phe Met Pro Glu Asp Ile Tyr Val Glu Trp Thr Asn Asn Gly Lys
            35                  40                  45

Thr Glu Leu Asn Tyr Lys Asn Thr Glu Pro Val Leu Asp Ser Asp Gly
        50                  55                  60

Ser Tyr Phe Met Tyr Ser Lys Leu Arg Val Glu Lys Lys Asn Trp Val
65              70                  75                  80

Glu Arg Asn Ser Tyr Ser Cys Ser Val Val His Glu Gly Leu His Asn
                85                  90                  95

His His Thr Thr Lys Ser Phe Ser Arg Thr
            100                 105

<210> SEQ ID NO 18
<211> LENGTH: 106
<212> TYPE: PRT
<213> ORGANISM: Mouse IgG2b

<400> SEQUENCE: 18

Ile Lys Gly Leu Val Arg Ala Pro Gln Val Tyr Thr Leu Pro Pro Pro
1               5                   10                  15

Ala Glu Gln Leu Ser Arg Lys Asp Val Ser Leu Thr Cys Leu Val Val
                20                  25                  30

Gly Phe Asn Pro Gly Asp Ile Ser Val Glu Trp Thr Ser Asn Gly His
            35                  40                  45

Thr Glu Glu Asn Tyr Lys Asp Thr Ala Pro Val Leu Asp Ser Asp Gly
        50                  55                  60

Ser Tyr Phe Ile Tyr Ser Lys Leu Asn Met Lys Thr Ser Lys Trp Glu
65              70                  75                  80

Lys Thr Asp Ser Phe Ser Cys Asn Val Arg His Glu Gly Leu Lys Asn
                85                  90                  95

Tyr Tyr Leu Lys Lys Thr Ile Ser Arg Ser
            100                 105

<210> SEQ ID NO 19
<211> LENGTH: 106
<212> TYPE: PRT
<213> ORGANISM: Mouse IgG3

<400> SEQUENCE: 19

Pro Lys Gly Arg Ala Gln Thr Pro Gln Val Tyr Thr Ile Pro Pro Pro
1               5                   10                  15

Arg Glu Gln Met Ser Lys Lys Lys Val Ser Leu Thr Cys Leu Val Thr
                20                  25                  30

Asn Phe Phe Ser Glu Ala Ile Ser Val Glu Trp Glu Arg Asn Gly Glu
            35                  40                  45

Leu Glu Gln Asp Tyr Lys Asn Thr Pro Pro Ile Leu Asp Ser Asp Gly
        50                  55                  60

Thr Tyr Phe Leu Tyr Ser Lys Leu Thr Val Asp Thr Asp Ser Trp Leu
65              70                  75                  80

Gln Gly Glu Ile Phe Thr Cys Ser Val Val His Glu Ala Leu His Asn
                85                  90                  95

His His Thr Gln Lys Asn Leu Ser Arg Ser
            100                 105

```
<210> SEQ ID NO 20
<211> LENGTH: 105
<212> TYPE: PRT
<213> ORGANISM: Human IgG1

<400> SEQUENCE: 20

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu
            100                 105

<210> SEQ ID NO 21
<211> LENGTH: 114
<212> TYPE: PRT
<213> ORGANISM: Human IgA

<400> SEQUENCE: 21

Ser Gly Asn Thr Phe Arg Pro Glu Val His Leu Leu Pro Pro Pro Ser
1               5                   10                  15

Glu Glu Leu Ala Leu Asn Glu Leu Val Thr Leu Thr Cys Leu Ala Arg
            20                  25                  30

Gly Phe Ser Pro Lys Asp Val Leu Val Arg Trp Leu Gln Gly Ser Gln
        35                  40                  45

Glu Leu Pro Arg Glu Lys Tyr Leu Thr Trp Ala Ser Arg Gln Glu Pro
    50                  55                  60

Ser Gln Gly Thr Thr Thr Phe Ala Val Thr Ser Ile Leu Arg Val Ala
65                  70                  75                  80

Ala Glu Asp Trp Lys Lys Gly Asp Thr Phe Ser Cys Met Val Gly His
                85                  90                  95

Glu Ala Leu Pro Leu Ala Phe Thr Gln Lys Thr Ile Asp Arg Leu Ala
            100                 105                 110

Gly Lys

<210> SEQ ID NO 22
<211> LENGTH: 112
<212> TYPE: PRT
<213> ORGANISM: Human IgE

<400> SEQUENCE: 22

Thr Ser Gly Pro Arg Ala Ala Pro Glu Val Tyr Ala Phe Ala Thr Pro
1               5                   10                  15

Glu Trp Pro Gly Ser Arg Asp Lys Arg Thr Leu Ala Cys Leu Ile Gln
            20                  25                  30

Asn Phe Met Pro Glu Asp Ile Ser Val Gln Trp Leu His Asn Glu Val
        35                  40                  45

Gln Leu Pro Asp Ala Arg His Ser Thr Gln Pro Arg Lys Thr Lys
    50                  55                  60

Gly Ser Gly Phe Phe Val Phe Ser Arg Leu Glu Val Thr Arg Ala Glu
```

-continued

```
                65                  70                  75                  80
Trp Glu Gln Lys Asp Glu Phe Ile Cys Arg Ala Val His Glu Ala Ala
                        85                  90                  95
Ser Pro Ser Gln Thr Val Gln Arg Ala Val Ser Val Asn Pro Gly Lys
                100                 105                 110

<210> SEQ ID NO 23
<211> LENGTH: 114
<212> TYPE: PRT
<213> ORGANISM: Human IgD

<400> SEQUENCE: 23

Arg Glu Pro Ala Ala Gln Ala Pro Val Lys Leu Ser Leu Asn Leu Leu
1               5                   10                  15
Ala Ser Ser Asp Pro Pro Glu Ala Ala Ser Trp Leu Leu Cys Glu Val
                20                  25                  30
Ser Gly Phe Ser Pro Pro Asn Ile Leu Leu Met Trp Leu Glu Asp Gln
                35                  40                  45
Arg Glu Val Asn Thr Ser Gly Phe Ala Pro Ala Arg Pro Pro Pro Gln
        50                  55                  60
Pro Gly Ser Thr Thr Phe Trp Ala Trp Ser Val Leu Arg Val Pro Ala
65                  70                  75                  80
Pro Pro Ser Pro Gln Pro Ala Thr Tyr Thr Cys Val Val Ser His Glu
                85                  90                  95
Asp Ser Arg Thr Leu Leu Asn Ala Ser Arg Ser Leu Glu Val Ser Tyr
                100                 105                 110
Val Thr

<210> SEQ ID NO 24
<211> LENGTH: 115
<212> TYPE: PRT
<213> ORGANISM: Human IgM

<400> SEQUENCE: 24

Pro Lys Gly Val Ala Leu His Arg Pro Asp Val Tyr Leu Leu Pro Pro
1               5                   10                  15
Ala Arg Glu Gln Leu Asn Leu Arg Glu Ser Ala Thr Ile Thr Cys Leu
                20                  25                  30
Val Thr Gly Phe Ser Pro Ala Asp Val Phe Val Gln Trp Met Gln Arg
                35                  40                  45
Gly Gln Pro Leu Ser Pro Glu Lys Tyr Val Thr Ser Ala Pro Met Pro
        50                  55                  60
Glu Pro Gln Ala Pro Gly Arg Tyr Phe Ala His Ser Ile Leu Thr Val
65                  70                  75                  80
Ser Glu Glu Glu Trp Asn Thr Gly Glu Thr Tyr Thr Cys Val Val Ala
                85                  90                  95
His Glu Ala Leu Pro Asn Arg Val Thr Glu Arg Thr Val Asp Lys Ser
                100                 105                 110
Thr Gly Lys
        115
```